United States Patent
Ouyang et al.

(10) Patent No.: US 9,468,367 B2
(45) Date of Patent: *Oct. 18, 2016

(54) METHOD AND APPARATUS FOR HYSTEROSCOPY AND COMBINED HYSTEROSCOPY AND ENDOMETRIAL BIOPSY

(71) Applicants: Xiaolong Ouyang, Palo Alto, CA (US); Paul D. Indman, San Jose, CA (US); Robert K. Deckman, San Bruno, CA (US); Shih-Ping Wang, Los Altos, CA (US)

(72) Inventors: Xiaolong Ouyang, Palo Alto, CA (US); Paul D. Indman, San Jose, CA (US); Robert K. Deckman, San Bruno, CA (US); Shih-Ping Wang, Los Altos, CA (US)

(73) Assignee: Endosee Corporation, Los Altos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/400,986

(22) PCT Filed: May 14, 2013

(86) PCT No.: PCT/US2013/040992
§ 371 (c)(1),
(2) Date: Nov. 13, 2014

(87) PCT Pub. No.: WO2014/031192
PCT Pub. Date: Feb. 27, 2014

(65) Prior Publication Data
US 2015/0164313 A1    Jun. 18, 2015

Related U.S. Application Data

(63) Continuation of application No. 13/474,429, filed on May 17, 2012, now Pat. No. 8,460,182.

(Continued)

(51) Int. Cl.
*A61B 1/00*        (2006.01)
*A61B 1/04*        (2006.01)
(Continued)

(52) U.S. Cl.
CPC ............ *A61B 1/303* (2013.01); *A61B 1/005* (2013.01); *A61B 1/00006* (2013.01);
(Continued)

(58) Field of Classification Search
CPC .... A61B 1/012; A61B 1/0125; A61B 1/015; A61B 1/018; A61B 1/04; A61B 1/05; A61B 1/06; A61B 1/0661; A61B 1/0676; A61B 1/0684; A61B 1/303; A61B 1/0008; A61B 1/00091; A61B 10/0291
USPC ....... 600/103, 104, 109, 117, 118, 127, 129, 600/131, 132, 135, 153, 155, 156, 157, 158, 600/159, 160, 179; 348/77
See application file for complete search history.

(56) References Cited

U.S. PATENT DOCUMENTS 4,201,199 A  *  5/1980  Smith .................... A61B 1/303
                                                    600/121
4,836,189 A       6/1989  Allred et al.
(Continued)

FOREIGN PATENT DOCUMENTS

WO    WO 2011/038310    3/2011
WO    WO 2012/060932    5/2012

OTHER PUBLICATIONS

International Search Report for International Application No. PCT/US13/40992, dated Oct. 17, 2013 (3 pages).
(Continued)

*Primary Examiner* — Thomas J Sweet
*Assistant Examiner* — William Chou
(74) *Attorney, Agent, or Firm* — Fish & Richardson P.C.

(57) ABSTRACT

Instruments and methods are described for performing hysteroscopy and/or combined hysteroscopy and endometrial biopsy. According to some embodiments, the handle, electronics and integrated display screen form a re-usable portion of the instrument while the fluid hub and cannula which includes a CMOS imaging module and LED lighting, form a single use portion of the instrument. The cannula is semi-flexible such that the operator can easily grasp the cannula at some intermediate point along the shaft (e.g. 5 inches from the distal tip) to bend and/or steer the cannula during use. According to some embodiments, the distal tip has a larger diameter than the shaft which has been found to improve fluid management during use in some applications.

11 Claims, 16 Drawing Sheets

Related U.S. Application Data

(60) Provisional application No. 61/646,887, filed on May 14, 2012, provisional application No. 61/664,143, filed on Jun. 25, 2012, provisional application No. 61/681,129, filed on Aug. 8, 2012, provisional application No. 61/672,733, filed on Jul. 17, 2012, provisional application No. 61/676,444, filed on Jul. 27, 2012, provisional application No. 61/692,701, filed on Aug. 23, 2012, provisional application No. 61/709,022, filed on Oct. 2, 2012, provisional application No. 61/709,033, filed on Oct. 2, 2012, provisional application No. 61/803,672, filed on Mar. 20, 2013, provisional application No. 61/803,664, filed on Mar. 20, 2013, provisional application No. 61/813,635, filed on Apr. 18, 2013, provisional application No. 61/818,341, filed on May 1, 2013, provisional application No. 61/667,341, filed on Jul. 2, 2012.

(51) Int. Cl.
  A61B 1/06    (2006.01)
  A61B 1/307   (2006.01)
  A61B 1/303   (2006.01)
  A61B 1/05    (2006.01)
  A61B 1/005   (2006.01)
  A61B 1/12    (2006.01)
  A61B 1/015   (2006.01)

(52) U.S. Cl.
  CPC ...... *A61B 1/00034* (2013.01); *A61B 1/00052* (2013.01); *A61B 1/00066* (2013.01); *A61B 1/00071* (2013.01); *A61B 1/00094* (2013.01); *A61B 1/00103* (2013.01); *A61B 1/00105* (2013.01); *A61B 1/00114* (2013.01); *A61B 1/00124* (2013.01); *A61B 1/015* (2013.01); *A61B 1/05* (2013.01); *A61B 1/06* (2013.01); *A61B 1/0676* (2013.01); *A61B 1/0684* (2013.01); *A61B 1/126* (2013.01); *A61B 1/307* (2013.01)

(56) References Cited

U.S. PATENT DOCUMENTS

| | | | |
|---|---|---|---|
| 5,484,422 A | 1/1996 | Sloane et al. | |
| 5,498,230 A | 3/1996 | Adair | |
| 5,506,912 A | 4/1996 | Nagasaki et al. | |
| 5,527,262 A | 6/1996 | Monroe et al. | |
| 5,591,119 A | 1/1997 | Adair | |
| 5,609,561 A | 3/1997 | Uehara et al. | |
| 5,637,074 A | 6/1997 | Andino et al. | |
| 5,662,586 A | 9/1997 | Monroe et al. | |
| 5,734,418 A | 3/1998 | Danna | |
| 5,751,341 A | 5/1998 | Chaleki et al. | |
| 5,873,816 A | 2/1999 | Kagawa et al. | |
| 5,879,289 A | 3/1999 | Yarush et al. | |
| 5,885,214 A | 3/1999 | Monroe et al. | |
| 5,902,230 A | 5/1999 | Takahashi et al. | |
| 5,993,378 A | 11/1999 | Lemelson | |
| 6,066,089 A | 5/2000 | Costello et al. | |
| 6,221,007 B1 | 4/2001 | Green | |
| 6,315,712 B1 | 11/2001 | Rovegno | |
| 6,348,035 B1 | 2/2002 | Takami | |
| 6,387,043 B1 | 5/2002 | Yoon | |
| 6,419,626 B1 | 7/2002 | Yoon | |
| 6,468,265 B1 | 10/2002 | Evans et al. | |
| 6,593,587 B2 | 7/2003 | Pease | |
| 6,652,453 B2 | 11/2003 | Smith et al. | |
| 6,717,166 B2 | 4/2004 | Pease | |
| 6,858,857 B2 | 2/2005 | Pease et al. | |
| 6,858,858 B2 | 2/2005 | Pease | |
| 6,929,600 B2 | 8/2005 | Hill | |
| 6,979,290 B2 | 12/2005 | Mourlas et al. | |
| 7,033,314 B2 | 4/2006 | Kamrava et al. | |
| 7,074,182 B2 | 7/2006 | Rovegno | |
| 7,099,078 B2 | 8/2006 | Spencer | |
| 7,214,183 B2 | 5/2007 | Miyake | |
| 7,365,768 B1 | 4/2008 | Ono et al. | |
| 7,384,308 B2 | 6/2008 | Boehnlein et al. | |
| 7,431,619 B2 | 10/2008 | Boehnlein et al. | |
| 7,520,854 B2 | 4/2009 | Sato | |
| 7,530,946 B2 | 5/2009 | Hartwick | |
| 7,581,988 B2 | 9/2009 | Boehnlein et al. | |
| 7,584,534 B2 | 9/2009 | Pease et al. | |
| 7,758,495 B2 | 7/2010 | Pease et al. | |
| 7,850,601 B2 | 12/2010 | Uchimura et al. | |
| 7,946,981 B1 | 5/2011 | Cubb | |
| 7,976,459 B2 | 7/2011 | Laser | |
| 7,979,689 B2 | 7/2011 | Watt et al. | |
| 8,004,560 B2 | 8/2011 | Sato et al. | |
| 8,007,433 B2 | 8/2011 | Iketani | |
| 8,022,979 B2 | 9/2011 | Miyamoto et al. | |
| 8,025,670 B2* | 9/2011 | Sharp | A61B 17/3421 128/842 |
| 8,033,993 B2 | 10/2011 | Amano et al. | |
| 8,133,169 B2 | 3/2012 | Nagase et al. | |
| 8,142,346 B2 | 3/2012 | Shoroji et al. | |
| 8,144,191 B2 | 3/2012 | Kawanishi et al. | |
| 8,157,726 B2 | 4/2012 | Melder | |
| 8,177,710 B1 | 5/2012 | Hosaka et al. | |
| 8,182,416 B1 | 5/2012 | Hosaka et al. | |
| 8,218,074 B2 | 7/2012 | Pease et al. | |
| 8,317,689 B1 | 11/2012 | Remijan et al. | |
| 8,356,527 B2 | 1/2013 | Hudson | |
| 8,382,665 B1 | 2/2013 | Fam | |
| 8,403,831 B2 | 3/2013 | Kishioka | |
| 8,416,291 B2 | 4/2013 | Carrey et al. | |
| 8,453,639 B2 | 6/2013 | Kim et al. | |
| 8,556,801 B2 | 10/2013 | Liu | |
| 8,574,151 B2 | 11/2013 | Mitsuhashi | |
| 8,581,971 B2 | 11/2013 | Miyamoto et al. | |
| 8,591,401 B2 | 11/2013 | Miyayashiki et al. | |
| 8,597,179 B2 | 12/2013 | Kokubo | |
| 8,638,361 B2 | 1/2014 | Tanabe et al. | |
| 8,641,605 B2 | 2/2014 | Shoroji et al. | |
| 8,656,697 B2 | 2/2014 | Zubiate et al. | |
| 2002/0077550 A1* | 6/2002 | Rabiner | A61B 17/22012 600/439 |
| 2003/0040659 A1 | 2/2003 | Kazakevich | |
| 2003/0195390 A1 | 10/2003 | Graumann | |
| 2004/0122327 A1 | 6/2004 | Belson et al. | |
| 2005/0075538 A1* | 4/2005 | Banik | A61B 1/00071 600/141 |
| 2005/0085690 A1 | 4/2005 | Tien | |
| 2006/0004258 A1 | 1/2006 | Sun et al. | |
| 2006/0155168 A1 | 7/2006 | Pease | |
| 2007/0030344 A1 | 2/2007 | Miyamoto et al. | |
| 2007/0038020 A1 | 2/2007 | Tien | |
| 2007/0167681 A1 | 7/2007 | Gill et al. | |
| 2007/0185379 A1 | 8/2007 | Newman et al. | |
| 2007/0225556 A1 | 9/2007 | Ortiz et al. | |
| 2007/0225561 A1 | 9/2007 | Watanabe et al. | |
| 2008/0045791 A1 | 2/2008 | Gal et al. | |
| 2008/0051628 A1 | 2/2008 | Pecherer et al. | |
| 2008/0058591 A1 | 3/2008 | Saadat et al. | |
| 2008/0058595 A1 | 3/2008 | Snoke et al. | |
| 2008/0108869 A1* | 5/2008 | Sanders | A61B 1/00105 600/109 |
| 2008/0195128 A1 | 8/2008 | Orbay et al. | |
| 2008/0200758 A1 | 8/2008 | Orbay et al. | |
| 2009/0030276 A1 | 1/2009 | Saadat et al. | |
| 2009/0082695 A1 | 3/2009 | Whitehead | |
| 2009/0105538 A1 | 4/2009 | Van Dam et al. | |
| 2009/0112058 A1 | 4/2009 | Kagawa | |
| 2009/0118575 A1 | 5/2009 | Ichikawa et al. | |
| 2009/0118580 A1 | 5/2009 | Sun et al. | |
| 2009/0167849 A1 | 7/2009 | Niida | |
| 2009/0196459 A1 | 8/2009 | Watt et al. | |
| 2009/0221873 A1 | 9/2009 | McGrath | |
| 2009/0318758 A1 | 12/2009 | Farr et al. | |
| 2010/0030020 A1 | 2/2010 | Sanders et al. | |

(56) References Cited

U.S. PATENT DOCUMENTS

| | | |
|---|---|---|
| 2010/0033563 A1 | 2/2010 | Boehnlein et al. |
| 2010/0033986 A1 | 2/2010 | Schober et al. |
| 2010/0128116 A1 | 5/2010 | Sato et al. |
| 2010/0185052 A1 | 7/2010 | Chang |
| 2010/0191050 A1 | 7/2010 | Zwolinski |
| 2010/0238278 A1 | 9/2010 | Rovegno |
| 2011/0009694 A1 | 1/2011 | Schultz et al. |
| 2011/0034773 A1 | 2/2011 | Ishigami et al. |
| 2011/0090331 A1 | 4/2011 | Draper |
| 2011/0112360 A1 | 5/2011 | Swann et al. |
| 2011/0112361 A1 | 5/2011 | Ishigami et al. |
| 2011/0130627 A1 | 6/2011 | McGrail et al. |
| 2011/0130632 A1 | 6/2011 | McGrail et al. |
| 2011/0137127 A1 | 6/2011 | Schwartz et al. |
| 2011/0160537 A1 | 6/2011 | Chen |
| 2011/0201884 A1 | 8/2011 | Kishioka |
| 2011/0270038 A1 | 11/2011 | Jiang et al. |
| 2011/0273556 A1 | 11/2011 | Lyons et al. |
| 2012/0099735 A1 | 4/2012 | Chen |
| 2012/0116160 A1 | 5/2012 | Nieman et al. |
| 2012/0130160 A1 | 5/2012 | Borrye |
| 2012/0209065 A1 | 8/2012 | Hosaka et al. |
| 2012/0209066 A1 | 8/2012 | Hosaka et al. |
| 2012/0209067 A1 | 8/2012 | Hosaka et al. |
| 2012/0277528 A1 | 11/2012 | Qiao |
| 2012/0289778 A1 | 11/2012 | Chan |
| 2012/0310045 A1 | 12/2012 | Hu et al. |
| 2012/0323073 A1 | 12/2012 | Azuma et al. |
| 2013/0041220 A1 | 2/2013 | Kutsuma |
| 2013/0046316 A1* | 2/2013 | Sullivan ............ A61B 10/0275 606/115 |
| 2013/0050455 A1 | 2/2013 | Yagi |
| 2013/0066151 A1 | 3/2013 | Chen |
| 2013/0066152 A1 | 3/2013 | Chen |
| 2013/0072754 A1 | 3/2013 | Okamoto et al. |
| 2013/0079594 A1 | 3/2013 | Motoki |
| 2013/0096376 A1 | 4/2013 | Takei et al. |
| 2013/0225924 A1 | 8/2013 | Simms et al. |
| 2013/0231533 A1 | 9/2013 | Papademetriou et al. |
| 2013/0244453 A1 | 9/2013 | Sakamoto |
| 2013/0253368 A1 | 9/2013 | Are et al. |
| 2013/0289347 A1 | 10/2013 | Ito et al. |
| 2013/0345503 A1 | 12/2013 | Friedrich |
| 2013/0345518 A1 | 12/2013 | Law et al. |
| 2014/0031621 A1 | 1/2014 | Liu |
| 2014/0039253 A1 | 2/2014 | Fang et al. |
| 2014/0073853 A1 | 3/2014 | Swisher et al. |

OTHER PUBLICATIONS

International Search Report for International Application No. PCT/US13/49074, dated Oct. 1, 2013 (1 page).

* cited by examiner

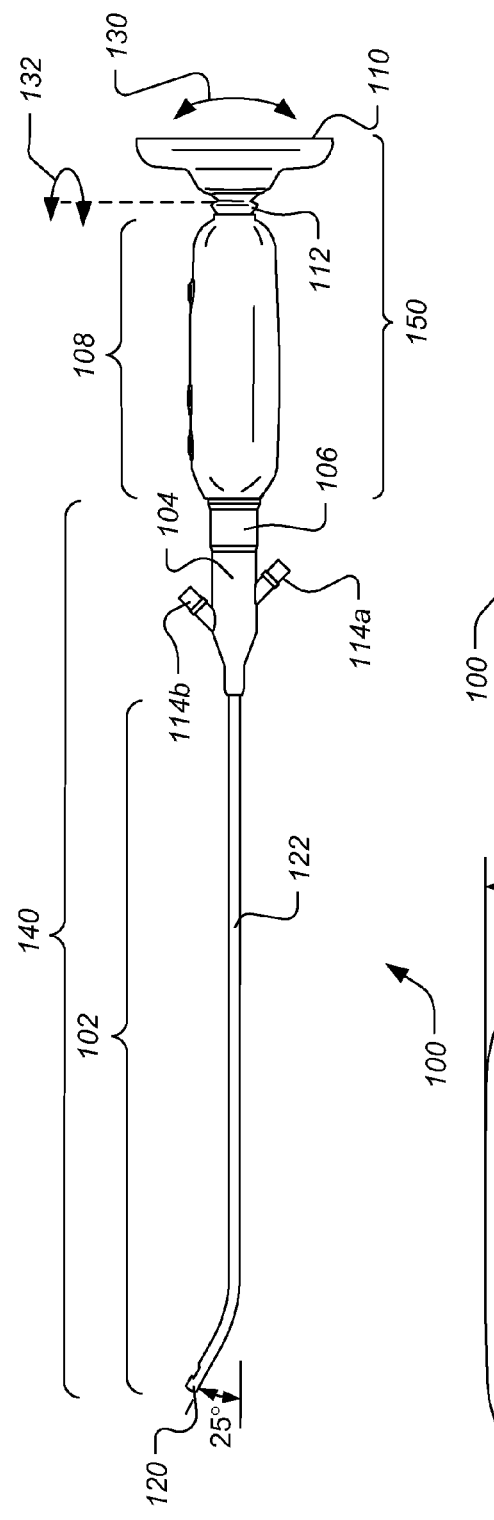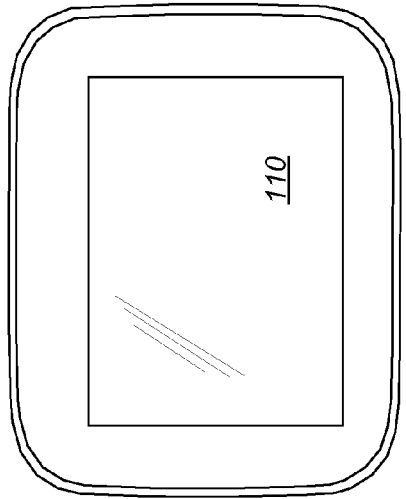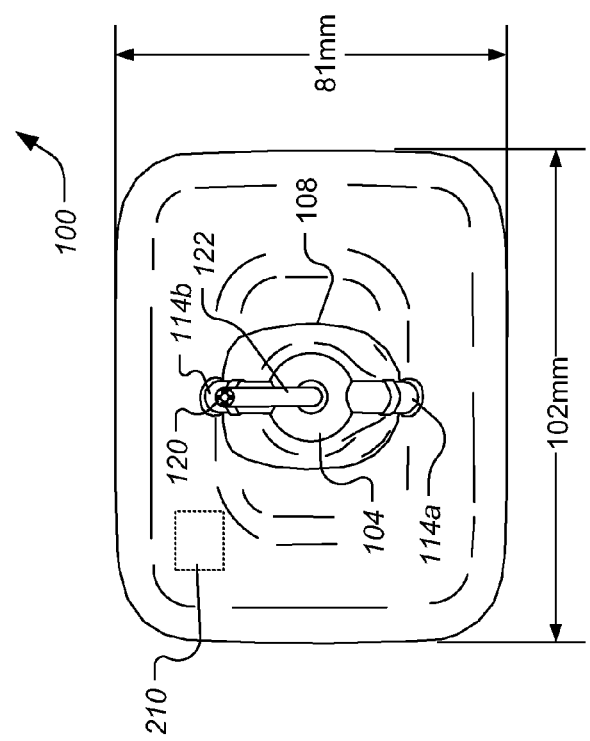

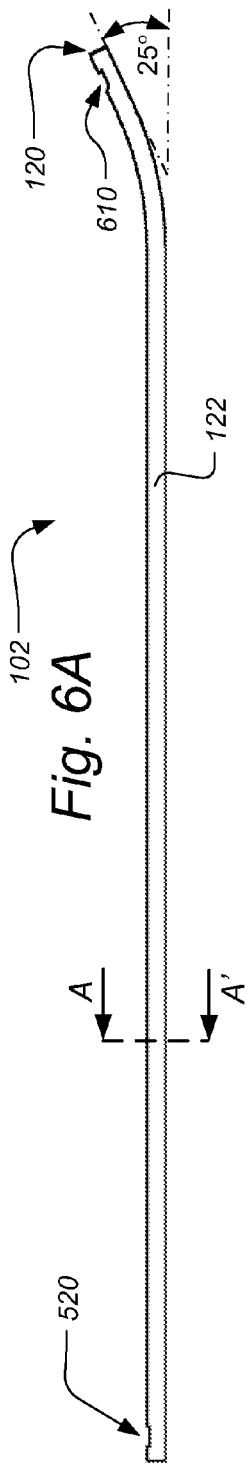
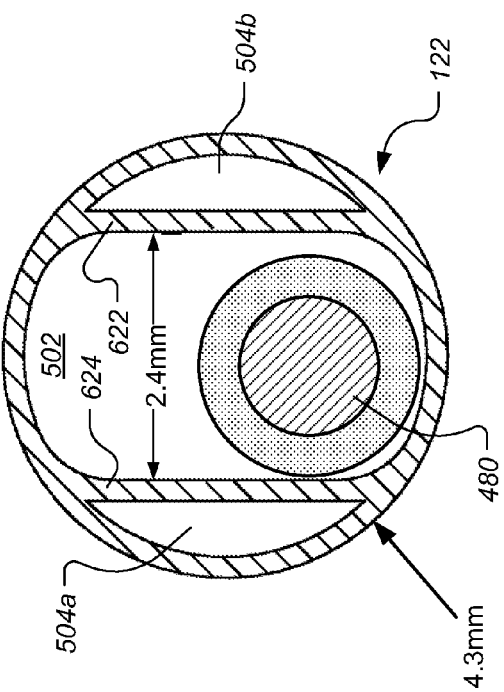
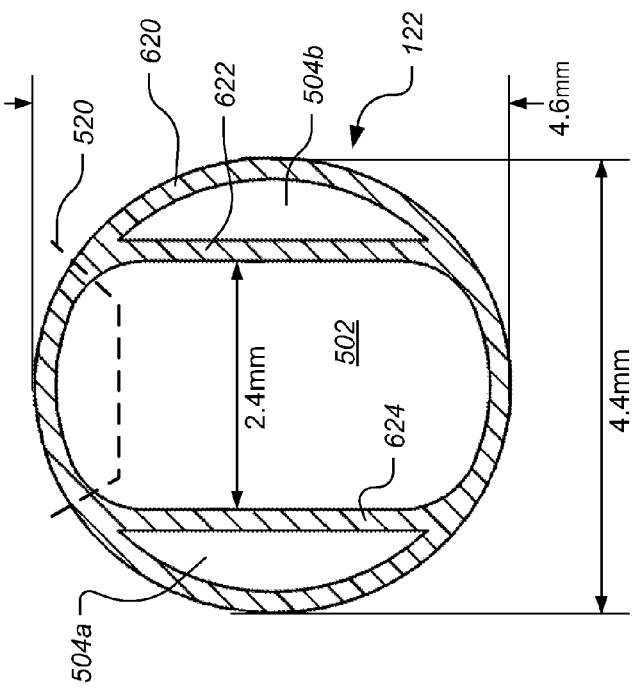

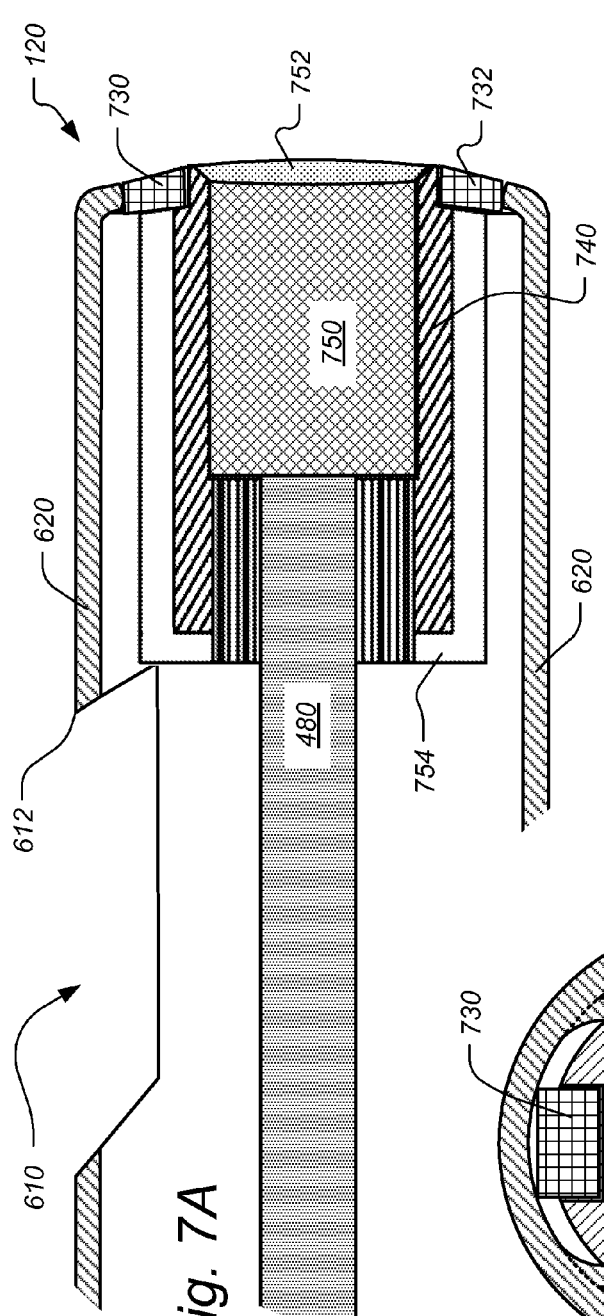
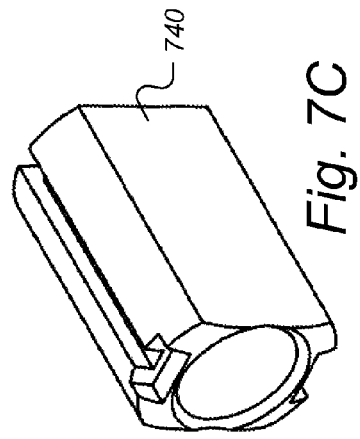
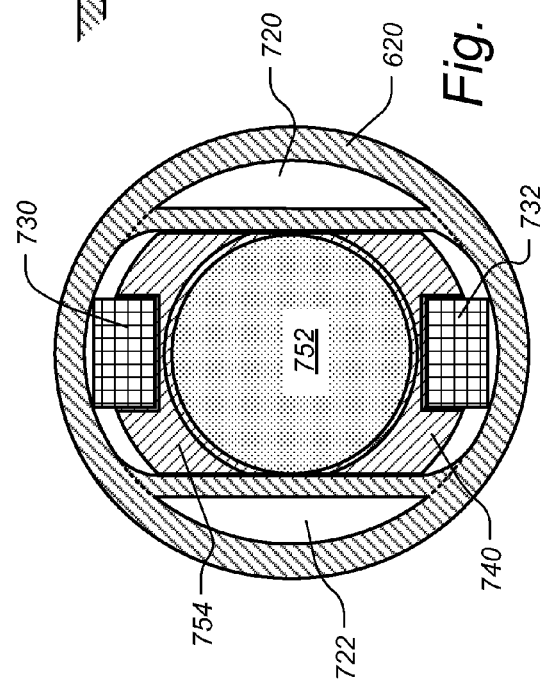

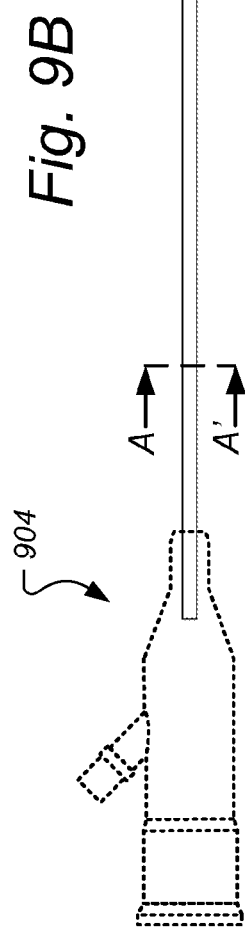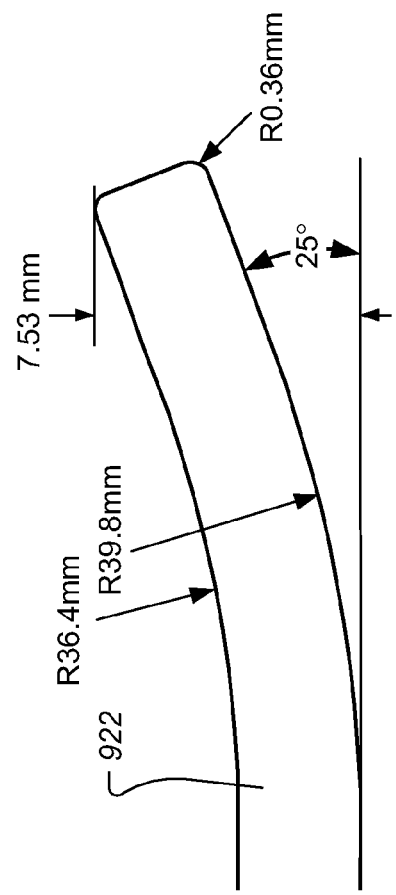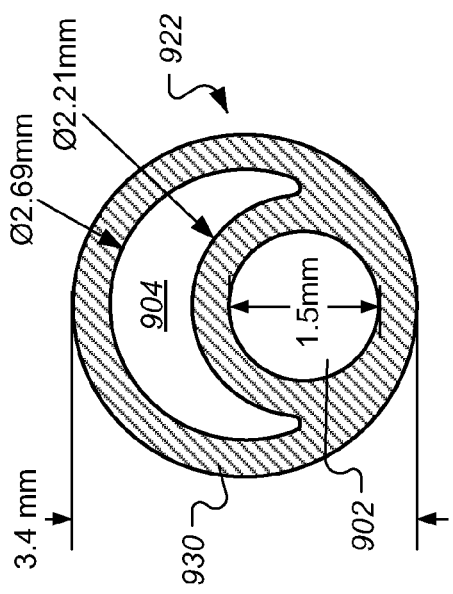
Fig. 9B
Fig. 9D
Fig. 9C (A-A')

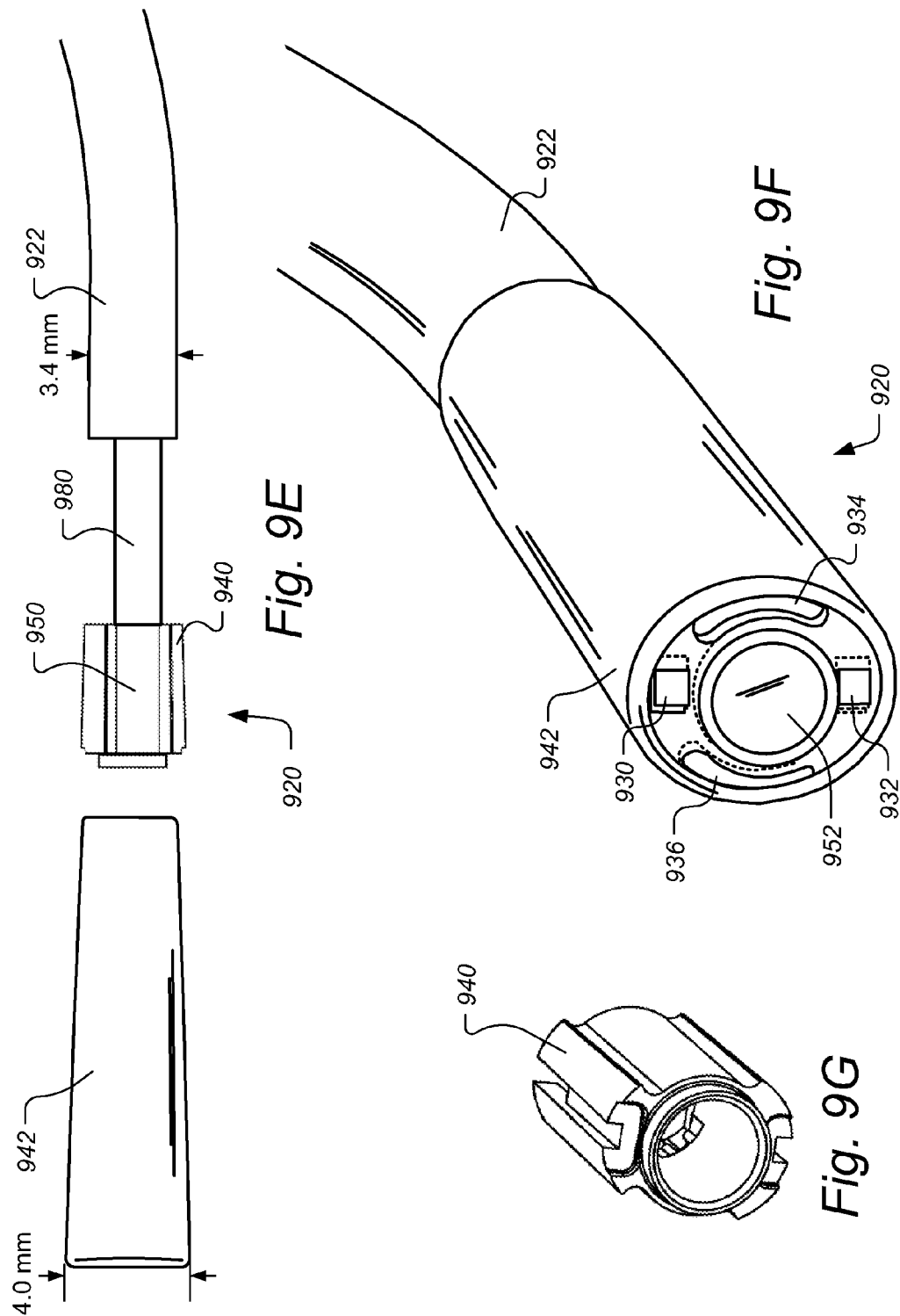

Plug alternative
(ENDO027)

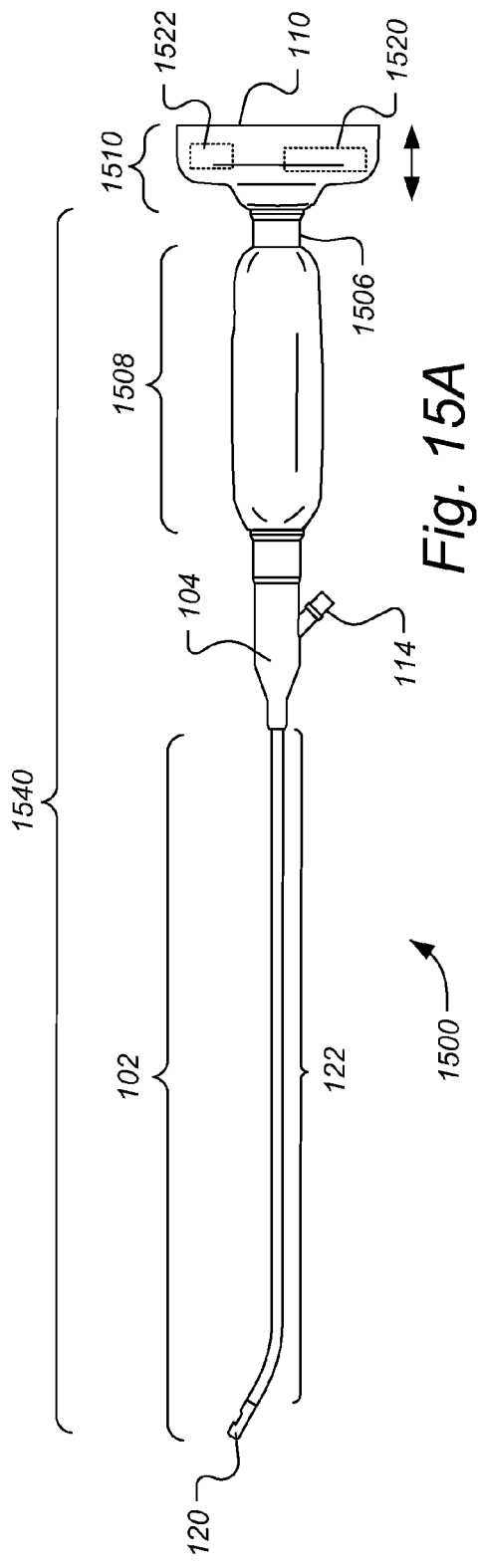
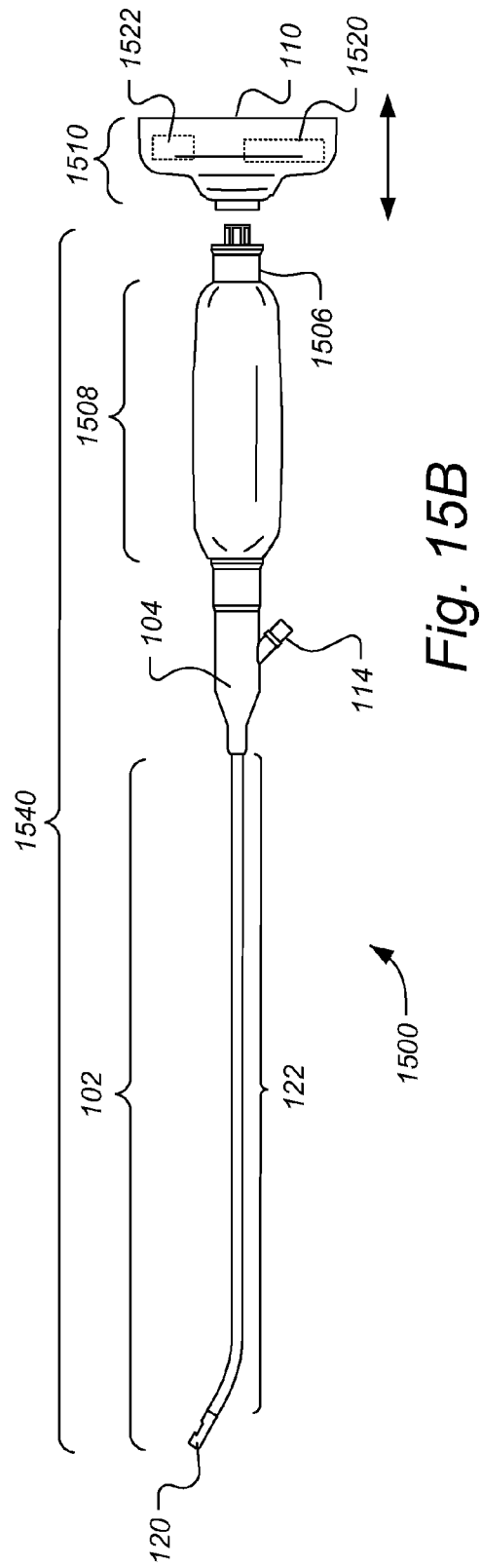
Fig. 15A
Fig. 15B

METHOD AND APPARATUS FOR HYSTEROSCOPY AND COMBINED HYSTEROSCOPY AND ENDOMETRIAL BIOPSY

REFERENCE TO RELATED APPLICATIONS

This patent application is a 371 U.S. National Application of PCT/US2013/040992, dated May 14, 2013, and claims the priority benefit of and incorporates by reference each of the following applications:

U.S. Prov. Ser. No. 61/646,887 filed May 14, 2012;
U.S. Prov. Ser. No. 61/667,341 filed Jul. 2, 2012;
U.S. Prov. Ser. No. 61/664,143 filed Jun. 25, 2012;
U.S. Prov. Ser. No. 61/672,733 filed Jul. 17, 2012;
U.S. Prov. Ser. No. 61/676,444 filed Jul. 27, 2012;
U.S. Prov. Ser. No. 61/681,129 filed Aug. 8, 2012;
U.S. Prov. Ser. No. 61/692,701 filed Aug. 23, 2012;
U.S. Prov. Ser. No. 61/709,022 filed Oct. 2, 2012;
U.S. Prov. Ser. No. 61/709,033 filed Oct. 2, 2012;
U.S. Ser. No. 13/474,429 filed May 17, 2012;
U.S. Prov. Ser. No. 61/803,664 filed Mar. 20, 2013;
U.S. Prov. Ser. No. 61/803,672 filed Mar. 20, 2013;
U.S. Prov. Ser. No. 61/813,635 filed Apr. 18, 2013; and
U.S. Prov. Ser. No. 61/818,341 filed May 1, 2013;

The subject matter of this patent specification relates to the subject matter of the following applications, each of which is incorporated by reference herein:

U.S. Ser. No. 12/911,297 filed Oct. 25, 2010;
U.S. Prov. Ser. No. 61/415,771 filed Nov. 19, 2010;
U.S. Prov. Ser. No. 61/418,248, filed Nov. 30, 2010;
U.S. Prov. Ser. No. 61/429,093 filed Dec. 31, 2010;
U.S. Prov. Ser. No. 61/431,316 filed Jan. 10, 2011;
U.S. Prov. Ser. No. 61/437,687, filed Jan. 30, 2011;
U.S. Prov. Ser. No. 61/444,098, filed Feb. 17, 2011;
U.S. Prov. Ser. No. 61/450,115, filed Mar. 7, 2011;
U.S. Prov. Ser. No. 61/453,533, filed Mar. 16, 2011;
U.S. Prov. Ser. No. 61/476,754, filed Apr. 18, 2011;
U.S. Prov. Ser. No. 61/482,200 filed May 3, 2011;
U.S. Prov. Ser. No. 61/482,309 filed May 4, 2011;
U.S. Prov. Ser. No. 61/485,601 filed May 12, 2011;
U.S. Prov. Ser. No. 61/490,029 filed May 25, 2011;
U.S. Prov. Ser. No. 61/494,400 filed Jun. 7, 2011;
U.S. Prov. Ser. No. 61/506,074 filed Jul. 9, 2011;
U.S. Prov. Ser. No. 61/515,092 filed Aug. 4, 2011;
U.S. Prov. Ser. No. 61/539,736 filed Sep. 27, 2011;
U.S. Prov. Ser. No. 61/544,280 filed Oct. 7, 2011;
U.S. Prov. Ser. No. 61/550,391 filed Oct. 22, 2011;
U.S. Prov. Ser. No. 61/555,470 filed Nov. 3, 2011;
U.S. Prov. Ser. No. 61/556,167 filed Nov. 4, 2011;
International Patent Appl. No. PCT/US11/51982 filed Sep. 16, 2011;
U.S. Prov. Ser. No. 61/570,816 filed Dec. 14, 2011;
U.S. Prov. Ser. No. 61/599,981 filed Feb. 17, 2012;
U.S. Prov. Ser. No. 61/600,593 filed Feb. 18, 2012;
U.S. Prov. Ser. No. 61/611,182 filed Mar. 15, 2012;
U.S. Prov. Ser. No. 61/623,376 filed Apr. 12, 2012; and
International Patent Appl. No. PCT/US2012/34698 filed Apr. 23, 2012.

The above-referenced provisional and non-provisional patent applications are collectively referenced herein as "the commonly assigned incorporated applications."

FIELD

The present invention generally relates mainly to a medical device for use in hysteroscopic examinations of the uterus. More particularly, some embodiments relate to a medical device having integrated visualization and endometrial sampling components.

BACKGROUND

Hysteroscopy, or direct vision of the inside of the uterus (referred to herein as the "uterine cavity" and/or "endometrial cavity"), has been shown to greatly improve diagnostic accuracy. Few gynecologists do office hysteroscopy, however, because of the complexity and expense of the equipment and supplies required. Conventional endoscopes are typically tethered and cumbersome to use. They require skilled staff to operate and maintain. This makes it especially difficult in time critical locations such as an emergency room, operating room, and other areas of a medical facility where multiple devices and instruments are being used simultaneously.

Office-based endometrial biopsy is a standard diagnostic procedure used by gynecologists. While efficacious in detection of cancer, endometrial biopsy frequently will not detect endometrial polyps, submucous myomas, and other endometrial pathology. While it is possible to take tiny biopsies through some hysteroscopes that have operating channels, the surgeon usually needs to remove the hysteroscope and then do an endometrial biopsy with a different instrument. The repeated insertion and removal of multiple instruments into the patient's uterine cavity can be uncomfortable for the patient and/or may prolong the time required to complete the hysteroscopy and endometrial sampling procedures compared to performing both procedures without the repeated insertion and removal of different instruments. And, such use of multiple instruments for the same inspection/biopsy procedure requires the expense and inconvenience of buying, stocking and sterilizing such instruments.

The subject matter claimed herein is not limited to embodiments that solve any specific disadvantages or that operate only in environments such as those described above. Rather, this background is only provided to illustrate one exemplary technology area where some embodiments described herein may be practiced.

SUMMARY

According to some embodiments, a low-cost medical instrument is described for examining a patient's uterus. The instrument includes a single-use portion configured to in a single insertion distend and image a patient's uterus. The single-use portion includes: an elongated conduit having a distal portion configured and dimensioned for insertion into the patient's uterus, and a proximal portion; a fluid connection port formed at the proximal portion of the conduit; one or more distal openings at the distal portion of the conduit configured to provide fluid from the conduit and into the uterus; an imaging system at the distal portion of the conduit configured to image the uterus and provide video signals; an illumination system at the distal portion of the conduit configured to illuminate the uterus at an illumination field viewed by the imaging system; and an electrical cable extending from a proximal end of the conduit to the imaging system and configured to carry video signals, control signals and electrical power. The instrument also includes a multiple-use portion having interior and exterior surfaces, the multiple-use portion being configured to be attached to the single-use portion for a single use and then detached after a single use, and to be re-used with a second single-use portion without sterilization of the interior surfaces. The multiple-use portion includes an integral image display that is electrically coupled with the imaging system at least in part by the electrical cable, the display being configured to display images provided by the imaging system for viewing by a user. The instrument also includes one or more seals configured to keep fluid in the conduit from contacting any of the interior surfaces of the multiple-use portion.

According to some embodiments, an integrated endoscopic instrument is described for examining a patient's uterus. The instrument includes an elongate member having a proximal end and a distal end. The elongate member is dimensioned and configured to facilitate insertion of the distal end through a patient's cervix and into the uterus. The elongate member is semi-flexible such that when fixedly held at 5 inches from the distal end and a 50 gram mass is applied two inches from the distal end the distal end bends in a downwards direction between 10 mm and 80 mm. The instrument further includes: an imaging system at the distal portion of the conduit configured to image the uterus and provide video signals; an illumination system at the distal portion of the conduit configured to illuminate the uterus at an illumination field viewed by the imaging system; a fluid opening positioned at the distal end of the elongate member to improve visual inspection using the electronic imaging module by delivering fluid to flow in a distal direction thereby clearing debris close to the imaging module; a handle that is configured and dimensioned to be grasped by a user's hand and manipulated by a user; and an integral image display that is electrically coupled with the imaging system at least in part an electrical cable. The display is configured to display images provided by the imaging system for viewing by the user.

According to some embodiments, an integrated endoscopic instrument is described for examining a patient's uterus. The instrument includes: an elongate member having a proximal end, a distal end, and a shaft extending from the distal end to the proximal end. The shaft houses a fluid channel and a plurality of electrical conductors. The conductors are configured to carry video and control signals. The shaft has a first outer diameter of less than 5 mm and the distal end has a second outer diameter greater than the first outer diameter. The instrument further includes: an imaging system at the distal portion of the conduit configured to image the uterus and provide video signals; an illumination system at the distal portion of the conduit configured to illuminate the uterus at an illumination field viewed by the imaging system; and a distal facing fluid opening at the distal end of the elongate member and in fluid communication with the fluid channel. The opening is positioned to improve visual inspection using the electronic imaging module by delivering fluid to flow in a distal direction thereby clearing debris close to the imaging module. The instrument further includes: a handle that is configured and dimensioned to be grasped by a user's hand and manipulated by a user; and an integral image display that is electrically coupled with the imaging system at least in part by at least some of the plurality of electrical conductors. The display is configured to display images provided by the imaging system for viewing by the user.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments and are therefore not to be considered limiting of the scope of this patent specification or the appended claims. The subject matter hereof will be described and explained with additional specificity and detail through the use of the accompanying drawings in which:

FIG. 1 is a left side view of a device for hysteroscopy and/or combined hysteroscopy and endometrial biopsy, according to some embodiments;

FIG. 2 is a distal end view of a device for hysteroscopy and/or combined hysteroscopy and endometrial biopsy, according to some embodiments;

FIG. 3 is a proximal end view of a device for hysteroscopy and/or combined hysteroscopy and endometrial biopsy, according to some embodiments;

FIGS. 6A-6F illustrate various aspects of a cannula for a device configured for combined hysteroscopy and endometrial biopsy, according to some embodiments;

FIGS. 7A-C show further detail of a distal tip of a device configured for combined hysteroscopy and endometrial biopsy, according to some embodiments;

FIGS. 9A-9G illustrate a single-use portion that includes a cannula configured for fluid-in flow and visualization, according to some embodiments;

FIGS. 15A-15C illustrate a device for hysteroscopy and/or combined hysteroscopy and endometrial biopsy having a single use cannula, fluid hub and handle, and a re-usable display screen, according to some embodiments.

DETAILED DESCRIPTION

Figure 4:
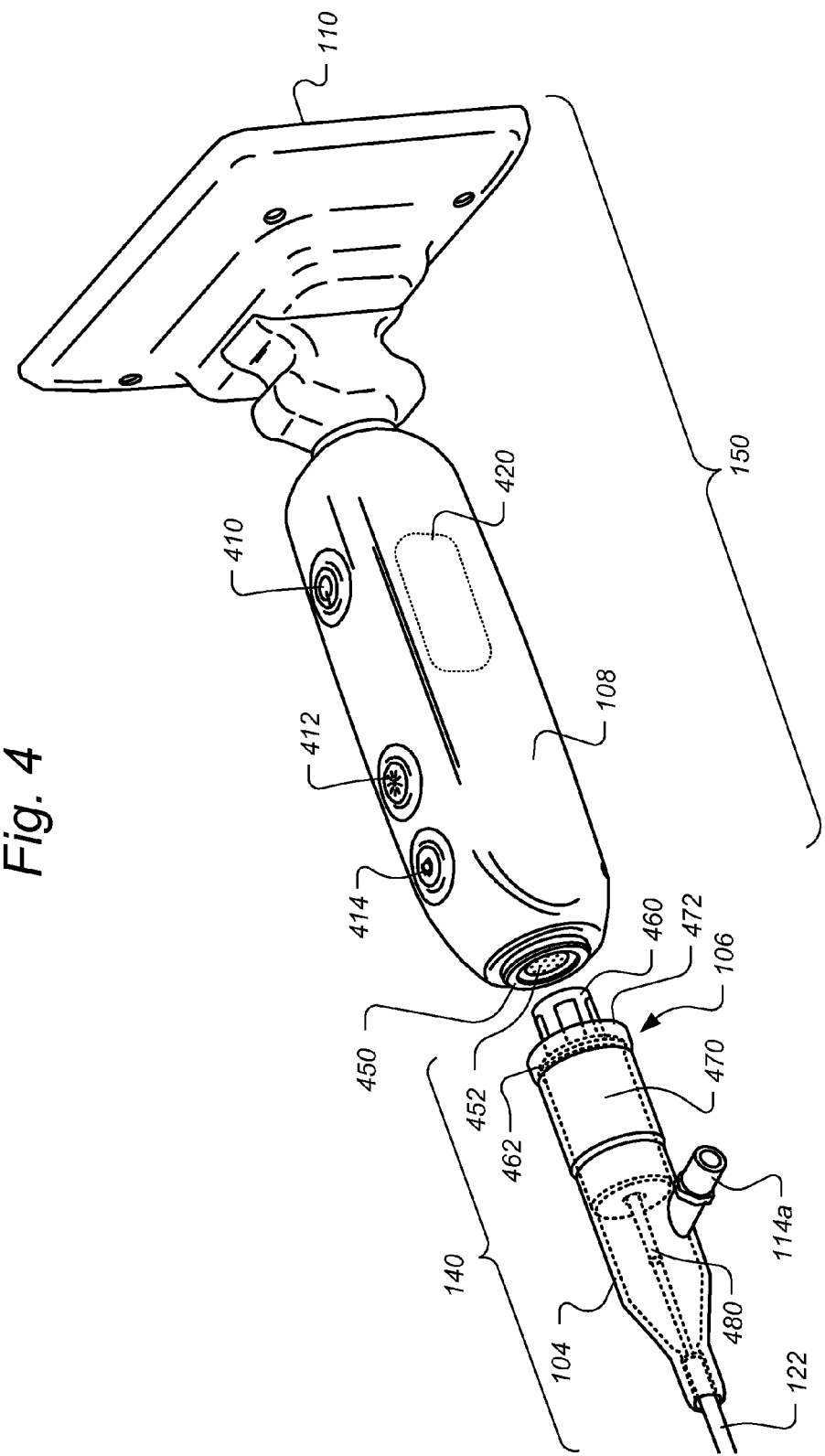
FIG. 4 is a perspective view of a device for hysteroscopy and/or combined hysteroscopy and endometrial biopsy, according to some embodiments.

A detailed description of examples of preferred embodiments is provided below. While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding work, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features or other described embodiments. Further, like reference numbers and designations in the various drawings indicate like elements.

FIG. 1 is a left side view of a device for hysteroscopy and/or combined hysteroscopy and endometrial biopsy, according to some embodiments. Many of the elements of the embodiments of hysteroscope 100 shown in FIG. 1 are the same as or similar to those discussed in the embodiments described in the commonly assigned incorporated applications, and such elements may not be described or may only briefly be described. It will also be appreciated that the aspects of the embodiments described in the commonly assigned incorporated applications may also apply to the embodiments described herein.

The device 100 is particularly advantageous for enabling a physician to perform an efficient combined hysteroscopic examination and an endometrial biopsy, although it is to be appreciated that other uses for hysteroscope 100 are within the scope of the present teachings. For example, as will be described in further detail, infra, the hysteroscope 100 can be fitted with other types of cannulas that are configured for other types of procedures such as hysteroscopy without biopsy. The hysteroscope 100 can bring about substantial efficiencies in terms of keeping equipment costs low and keeping the time required to perform the procedure modest, while at the same time providing the opportunity for better endometrial sample quality over conventional "blind" endometrial sample collection methods. Hysteroscope 100 includes a sampling cannula 102, fluid hub 104, sliding connector 106, handle body 108, display mount 112 and display 110. The biopsy sampling cannula 102 is made of a distal tip 120 and a shaft 122. The fluid hub in this case includes two fluid ports 114a and 114b. In the example shown in FIG. 1, fluid port 114a is configured to deliver fluid into the device and thus into the uterus, and fluid port 114b is configured to apply suction to extract fluid and tissue samples from the uterus. As shown, the shaft 122 is curved near its distal end, for example having a 25 degree bend as shown. According to some embodiments, a bend of between 15 and 35 degrees near the distal end has been found to be suitable for many applications. The distal tip 120 includes a video camera assembly, lighting elements and fluid ports for in-flow (i.e. out of the device 100 and into the patient) and out-flow (i.e. into the device 100 and out of the patient). A sampling port on the upper side of the distal tip 120 also includes a cutting portion, which aids in tissue sample collection, as described in more detail below. According to some embodiments, the outer shell of tip 120 and shaft 122 are constructed of the same material, for example a heat and UV stabilized nylon 12 grade for tube extrusion such as Grilamid® L25. According to some embodiments the display 110 is a touch-screen display, and is able to tilt upwards and downwards by, for example, about 60 degrees each (total range of motion of 120 degrees), and pivot, or "pan" left and right by, for example, 45 degrees each (total range of motion 90 degrees) as shown by arrows 130 and 132 respectively. According to some embodiments, the cannula 102 (including the camera assembly, LED lighting and fluid ports integrated into the distal tip 120), fluid hub 104 and sliding connector 106 together form a single-use portion 140, which is designed for a single-use. According to these embodiments the single-use portion 140 is delivered to the medical practitioner in pre-sterilized package and are intended to be disposed of after a single-use, and the handle 108 and display 110 form a re-usable portion 150, which is designed to be re-used many times.

According to some embodiments, the device 100 shown for example in FIG. 1 is a hand-held, compact single use endoscope. In these cases, endoscope 100 is provided in a sterile package, so is ready for immediate use without requiring any preparation for diagnostic or therapeutic procedures. According to some embodiments the single use device 100 needs no sophisticated connectors such that the entire endoscope is supplied in a sterile package ready for use.

FIG. 2 is a distal end view of a device for hysteroscopy and/or combined hysteroscopy and endometrial biopsy, according to some embodiments. The tip 120 and shaft 122 can be seen, as well as the fluid hub 104, fluid ports 114a and 114b, as well as handle body 108. Also shown, according to some embodiments is photo/video processing circuitry 210 that can be used to enhance or otherwise manipulate standard video signals and/or images received from the camera module in tip 120. According to some embodiments, in FIG. 2 as in other figures herein, various dimensions are shown that have been found to be suitable for many applications, but those skilled in the art may vary those dimensions without departing from the teachings of this patent specification.

FIG. 3 is a proximal end view of a device for hysteroscopy and/or combined hysteroscopy and endometrial biopsy, according to some embodiments. Touch-sensitive screen 110 is preferably 3.5 inches (diagonally) in size.

FIG. 4 is a perspective view of a device for hysteroscopy and/or combined hysteroscopy and endometrial biopsy, according to some embodiments. In FIG. 4 the single-use portion 140 is shown disconnected from the re-usable portion 150. The sliding connector 106 is shown and has an outer shell 470 that includes a lip 472 that fits over an o-ring seal 462 and a protruding mating portion 450 of the handle assembly 108. Multiple similar seals can be provided along the length of connector 106 to further isolate handle 108 from patient matter and/or fluids that could otherwise contaminate and/or cause connection failure such as electrical failures on handle 108. Also within connector 106 is a seal which forms a barrier between the proximal end of electrical cable 480 and fluid and/or patient matter. The cable 480 carries video signals and control signals between the camera module and LEDs at distal tip 120 to connection pins housed within sleeve 460. The sleeve 460 fits into a closed channel on the handle 108 while the connection pins mate with pin receptacles 452 as to form electrical connections with the pins.

Also visible in FIG. 4 is ON/OFF button 410 is used to toggle the device 100 on or off. According to some embodiments, the power ON/OFF button 410 is backlit using two differently colored LEDs to indicate the status of rechargeable battery 420 to the user. For example, green backlighting can be used to indicate the battery level is OK and red backlighting can be used to indicate the battery 420 is low. According to some embodiments the capacity of battery 420 is about 2500 mAh. According to some embodiments, the LED lighting of button 412 can also be used to indicate battery charging status during re-charging of the battery 420 from an external power source. In this case, the backlighting LED shows red while charging the battery and green when the battery 420 is fully charged. According to some embodiments, the ON/OFF button 410 doubles as a "home" button, such that a shorter press, such as 1 second or less, of button 410 brings up a home screen menu on the display 110.

LED brightness control button 412 is used to control the brightness of the LEDs on the distal tip 120. According to some embodiments a total of four different LED illumination levels has been found to be suitable and the single button 412 controls the level by cycling through the levels, changing the illumination level with each button press. The Snap/Video button 414 is used to capture still images and/or video from the camera in tip 120. According to some embodiments, pressing Snap/Video button 414 for three seconds or less captures a single still photo, while pressing button 414 for longer than three seconds starts video recording. When video is being recorded, a single press of button 414 stops video capture. According to some embodiments, an audible acknowledgement signal is associated with presses of the buttons 410, 412 and 414. For example, a single "beep" is sounded when any of the buttons except for double beeps when either the Snap/Video button 414 or an OK software button is pressed.

It has been found that providing dedicated hardware buttons on the handle itself have several advantages over touch-screen implemented "soft buttons" and/or hardware buttons located in locations other than the handle. The handle located hardware buttons, such as shown in FIG. 4, allow for one-handed operation as well as for operation with gloved and/or wet hands. With one-handed operation, a user can use a single hand to both manipulation of scope and operate buttons such as the "snap" and/or the "LED" buttons. The user's other hand is then free for other procedures or for manipulating the cannula (e.g. bending of cannula and/or steering the cannula). In other examples, for some reason the user's other hand may not be sterile. Furthermore, it has been found that the use of touch-screen implemented soft buttons on touch screen display 110 may not reliably work with gloved and/or wet fingers.

Figure 5:
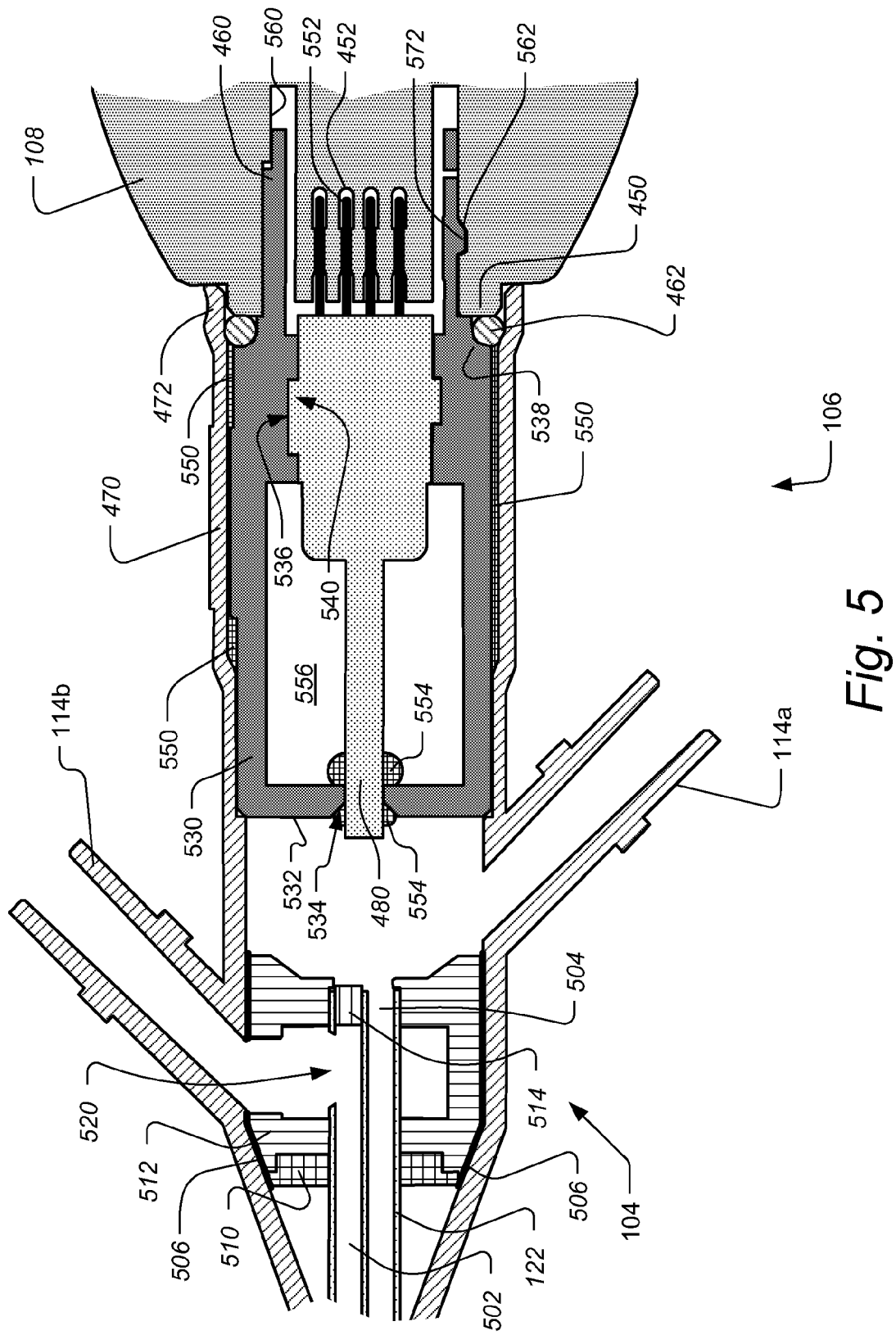
FIG. 5 is a cross section showing details of a sealed sliding connector for a device for hysteroscopy and/or combined hysteroscopy and endometrial biopsy, according to some embodiments.

FIG. 5 is a cross section showing details of a sealed sliding connector for a device for hysteroscopy and/or combined hysteroscopy and endometrial biopsy, according to some embodiments. The sliding connector 106 is shown here with an outer shell 470 that includes a lip 472 that fits over an o-ring seal 462 and a protruding mating portion 480 of the handle assembly 108. Other seals can be provided along the length of connector 106 to further isolate handle 108 from patient matter and/or fluids that could otherwise contaminate and/or cause connection failure such as electrical failures on handle 108. The cable 480 carries video signals, control signals and electrical power between the camera module and LEDs at distal tip 120 to connection pins housed within sleeve 460. The sleeve 460 fits into a closed channel on the handle 108 while the connection pins 552 mate with pin receptacles 452 as to form electrical connections the pins. The sliding connector 106 includes a barrier 530 that fits tightly inside outer shell 470. According to some embodiments, a transparent sealing glue 550 is applied between the barrier 530 and shell 470 as shown in FIG. 5. Barrier 530 terminates at its proximal end in an extended sleeve 460 that fits into a closed channel 560 in handle 108 such that an outwardly facing bump 572 releasably fits into an inward facing depression 562 in channel 560. Barrier 530 further includes a distal portion that terminates in a first seal 532 having an opening 534 through which cable 480 passes. An intermediate portion of barrier 530 provides an additional seal by including an inner indentation 536 tightly enveloping a radial projection 540 of the proximal portion of cable 480. Barrier 530 further includes at its proximal portion a lip 538 that helps form another additional seal by bearing against o-ring 462 to further help ensure that fluid and tissue matter will not reach interior portions of handle 108 when the instrument is in use. According to some embodiments glue 554 is used to enhance the seal between barrier 530 and cable 480 as shown. According to some other embodiments, glue 554 additionally is used to mostly or fully fill the inner void 556 of barrier 530 as well. According to some embodiments, other techniques and/or combinations of techniques are used to implement the fluid barrier between the single use portion 140 and multi-use portion 150 of the device 100. For example, the seal or seals can be implemented using structures such as gaskets, caps, o-rings alone, with each other and/or in combination with glues and/or ultrasonic welding or bonding techniques.

Also visible in FIG. 5 is a fluid cap 510 and gasket 512 that are shaped and positioned to provide fluid communication between a cutout 520 in shaft 122 to fluid port 114*b*. For simplicity, the shaft 122 is shown with two fluid lumens. One fluid lumen 502 is in fluid communication with fluid port 114*b* and the other fluid lumen 504 is in fluid communication with fluid port 114*a*. A plug 514 is inserted in the end of lumen 502 to prevent fluid communication between lumen 502 and fluid port 114*a*. As is described infra, the actual cross section of the shaft 122 can be of other layouts and the cut-outs and/or plug shapes and locations depends on the design of the fluid hub and shaft being used. According to some embodiments, transparent sealing glue 506 is used between the outer shell of the fluid hub 104 and the cap 510 and gasket 512.

According to some embodiments the fluid barrier and sealing can be implemented by one or more ultrasonic welding processes. In these cases, the outer shell 470 is manufactured as two pre-molded halves (for example split along the central longitudinal axis). Assembling two halves enhances the ability to effectively and evenly apply the glue, such as glue 506 and glue 550. According to some embodiments, certain interior structural components, such as barrier 530, gasket 512 and/or cap 510, are bonded or welded ultrasonically directly to the shell 470. In such cases, the use of glue 506 and/or 550 can be eliminated or at least supplemented. According to some embodiments, a some or all of barrier 530 is also manufactured as two halves. During assembly the placement of the glue 554 is more easily and robustly applied to form a seal between opening 534 of barrier 530 and cable 480.

Figure 6D:
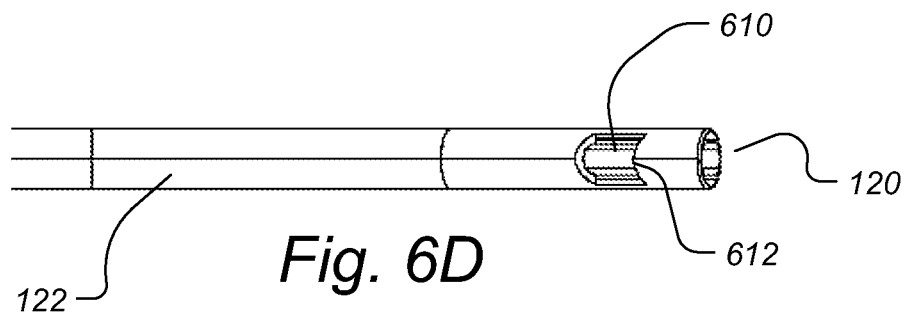

FIGS. 6A-6F illustrate various aspects of a cannula for a device configured for combined hysteroscopy and endometrial biopsy, according to some embodiments. FIG. 6A shows a right side view of shaft 122 of cannula 102, such a shown in device 100 of FIG. 1. The shaft 122 configured for hysteroscopy using LED lighting, camera module and forward facing fluid ports on distal tip 120 as well as for taking biopsy tissue samples using a sampling port 610. The proximal end of shaft 122 includes a cutout section 520 for making fluid communication with one of the fluid lumens to a fluid port located in a fluid hub. By constructing the cannula shaft 122 from a single piece of extruded tubing, the need for additional tubes is eliminated, and it has been found that assembly yield rates are significantly improved. According to some embodiments the shaft 122 is constructed of a heat and UV stabilized nylon 12 grade for tube extrusion such as Grilamid® L25. FIG. 6B is a cross sectional view along A-A', according to some embodiments. In this case, the shaft 122 is elliptical such that it is slightly taller than it is wide. In the embodiment shown, the outer walls 620 and inner walls 622 and 624 are 0.008" thick and define a central lumen 502 and two side lumens 504a and 504b. According to some embodiments, each of the side lumens 504a and 504b have a cross sectional area of 1.22 mm². Also shown in FIG. 6B is the approximate location of the cutout 520. As can be seen the central lumen 502 can be connected to a fluid port via the cutout 520. According to some embodiments, the central lumen 502 is used for both the electrical cable 480 (shown in FIG. 4), as well as for drawing fluid ("outflow") so as to aid in taking tissue samples by being in fluid communication with fluid port 114b (shown in FIG. 5). The two side lumens 504a and 504b are both in fluid communication with the in-flow fluid port 114a. Note that according to this embodiment, the plug 514 shown in FIG. 5 would be used to plug the proximal end of central lumen 502, and the plug 514 has a hole for allowing cable 480 to pass through it. On the distal end of the shaft 122, the two side lumens 504a and 504b are each in fluid communication with a forward facing fluid port on distal tip 120, as shown in FIG. 7B, infra. FIG. 6C shows another example of a cross section of shaft 122 which in this case is round, having a outer diameter of 4.3 mm. Also visible in FIG. 6C is the electrical cable 480 which is enclosed in a waterproof jacket.

Figure 6E:
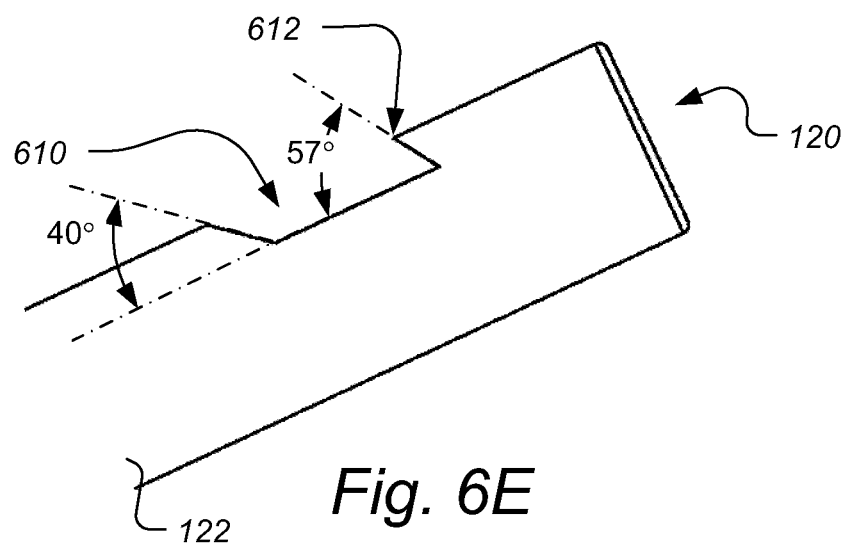
Figure 6F:
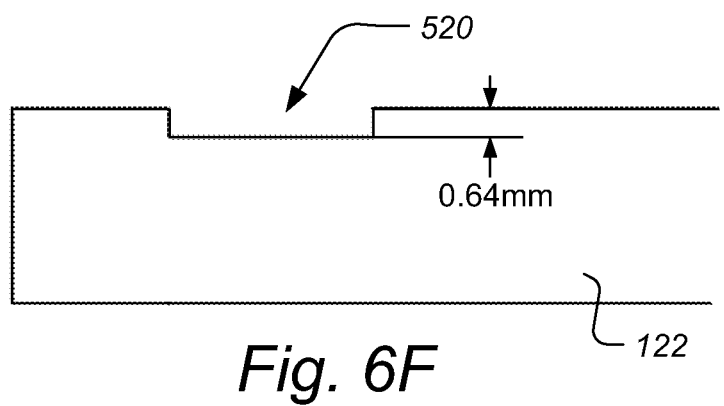

FIG. 6D is a top view of the distal area of shaft 122, according to some embodiments. Near the distal tip 120, the sampling port 610 includes a cutting edge 612, which is sharp and positioned so as to facilitate collection of the endometrial sample by scraping. FIG. 6E is a side view showing further details of the shape of distal tip 120 of shaft 122, according to some embodiments. FIG. 6F shows details of the proximal end of shaft 122 including the cut out 520, according to some embodiments.

FIGS. 7A-C show further detail of a distal tip of a device configured for combined hysteroscopy and endometrial biopsy, according to some embodiments. Visible in FIG. 7A, on top side of distal tip 120 is the sampling port 610 used to draw fluid out of the patient's uterus as well as collect tissue. On the distal end of the tip 120 is lens sensor stack 750. According to some embodiments, lens sensor stack 750 consists of a lens set (which includes an iris) precisely positioned on top of a CMOS sensor. Lens sensor stack 750 is held together by a plastic (or in some embodiments stainless steel) housing or holder block 740. Glass 752 in some embodiments is simply a protective glass cover, and according to some other embodiments is the first element of the lens set. Glass 752 is coated with hydrophobic or hydrophilic film. The lens sensor stack 750, holder 740 and glass 752 together are referred to herein as camera module 754. According to some embodiments the camera module 754 also includes a shield (not shown) to block direct entry of light from LEDs 730 and 732 into the sensor lens stack 750. According to some embodiments, camera module 754 is about 2.2 mm×2.2 mm in cross sectional size.

According to some embodiments, the CMOS sensor within lens sensor stack 750 includes a low voltage color CMOS image sensor core, image sensor processing and image output interface circuitry on a single chip such as the OmniVision 7675. According to some other embodiments, an additional chip can be used to carry out video processing which is mounted on the same mini-PCB as the CMOS sensor. By providing integrated digital video processing within the sensor module, all video processing can be performed directly on the same PCB as the CMOS sensor, or on the same substrate in which the CMOS is formed such that the imaging plane of the CMOS and the plane along which the video processing circuits extend substantially coincide. In this example, the video signal from the sensor module can be in any suitable video format, such as NTSC, PAL, or another common video format, so that no further video processing would be required to drive widely available displays for common video formats such as TV displays, tablets, computers and hospital workstations.

Two LEDs 730 and 732 are positioned above and below and mounted to the camera module 754 to evenly illuminate the uterine tissue for visual inspection. According to some embodiments each of the LEDs 730 and 732 are about 1.0 mm×0.5 mm in frontal area. One problem in performing visual inspections of endometrial tissues, and particularly in situations where the endometrial medium, consisting of free tissue, loosely attached tissue and/or fluid, is relatively thick, is that light reflected from tissue particles suspended close to the lens can appear overly-bright and therefore impair imaging of other tissue surfaces. As can be seen in FIG. 7B, which is a front view of distal tip 120, two forward facing fluid ports, 720 and 722 are provided to allow fluid to exit the tip and tend to push suspended particulate matter away from the camera so as to enhance image and video capture by camera module 754. In some cases some tissue debris may collect on the distal surface such that imaging would be impaired in such cases the forward facing ports are useful in clearing away such collected tissue. Also it has been found that the forward facing ports are helpful in aiding insertion of the cannula in many cases as the fluid provides lubrication as well as a partial distending of tissues just ahead of the distal tip during insertion. Since the forward facing ports improve visualization, the risk of accidental damage to the uterus is greatly reduced. FIG. 7C is a perspective view of the holder block 740 which according to some embodiments is made of a suitable plastic material, such as liquid crystal polymer. The distal tip 120 in this case includes separated fluid channels for fluid in-flow and out-flow. In particular, the central fluid lumen 502 is in fluid communication with the sampling port 610, and is blocked via the holder block 740 from being in fluid communication with the forward facing ports 720 and 722. Similarly, the two side fluid lumens 504a and 504b are in fluid communication with forward facing fluid ports 722 and 720, respectively.

Figure 8:
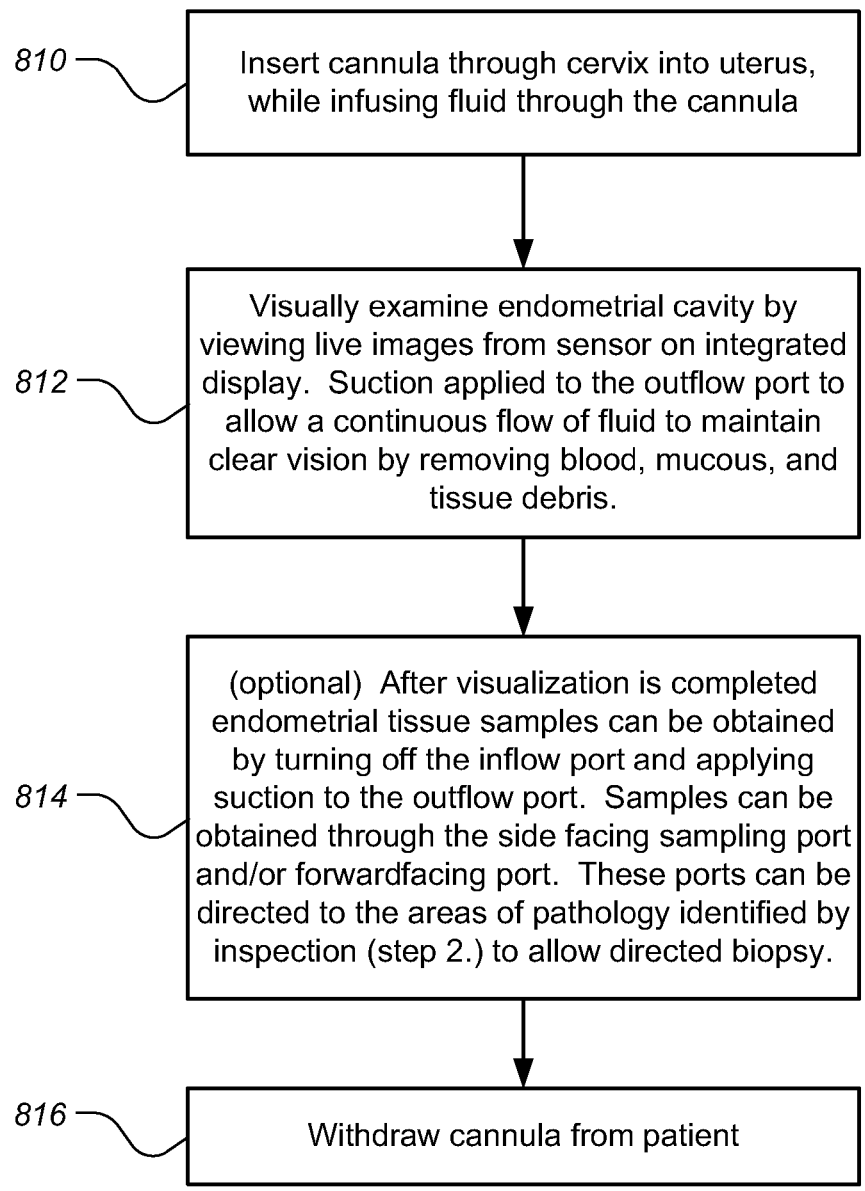
FIG. 8 is a flow chart illustrating aspects of using a multi-lumen cannula with simultaneous in-flow and out-flow for a hysteroscopy procedure, according to some embodiments.

In performing a hysteroscopy procedure, it has been found that providing a device that has separated fluid flow channels for in-flow and out-flow has certain benefits including allowing for simultaneous in-flow and out-flow. FIG. 8 is a flow chart illustrating aspects of using a multi-lumen cannula with simultaneous in-flow and out-flow for a hysteroscopy procedure, according to some embodiments. In step 810, the cannula 102 is inserted through the cervix into the patient's uterus while in-flowing fluid through the in-flow lumen(s) such as lumens 504a and 504b shown in FIG. 6B or 6C, and through forward facing ports such as ports 720 and 722 shown in FIG. 7B. In step 812, the endometrial cavity is visually examined by viewing live images from the sensor in the camera module 754 (shown in FIG. 7A) and on the integrated display 110 shown in FIGS. 1 and 3. Suction is applied to the out-flow port (port 114b, shown in FIGS. 1, 2 and 5) to allow for a continuous flow of fluid which maintains clear visibility by removing blood mucus and other opaque material such as tissue debris. In and optional step 814, after visualization is completed, one or more endometrial tissue samples can be obtained by turning off the inflow port and applying suction to the outflow port. Samples can be obtained from a side facing port such as port 610 shown in FIGS. 6A, 6D and 6E. The location of the biopsy sampling be based on the areas of pathology identified by the visual inspection step 812 to allow for a directed biopsy. Additionally according to some embodiments where conditions allow it, visualization can continue during step 814 allowing for further visual confirmation of the location of the biopsy. In step 816 the cannula is withdrawn from the patient.

It has been found that it is very useful to provide the device 100 as divided into two portions: a single use portion, such a portion 140 in FIG. 1, and a re-usable portion 150 in FIG. 1. According to some embodiments, the re-usable portion includes the handle and integrated display, where some of the more costly components (such as the display) as well as some of the components that may be difficult or impractical to be re-sterilized (such as some of the electronic components) are located. According to some embodiments the separable design shown allows for different types of single-use portions to be provided that each are configured to operate with a single re-usable portion. Examples of different types of single use portions include cannulas having different port configurations (including the presence or absence of a side-facing port), different fluid hub layout configurations (including the number of fluid ports), as well as cannulas having different bend locations and amount, as well as different flexibility characteristics. The selection of which cannula design to use can be a matter of preference by the user but can also be influenced by anatomical variables, as well as what type of procedure is being performed. For example, according to some embodiments at least three main types of single-use cannula are provided that are all compatible with a re-usable handle and display portion: (1) a diagnostic cannula having in-flow capability for distention and visualization, but without a dedicated out-flow port for sampling; (2) a combined visualization and biopsy cannula which is configured for both visualization and taking tissue samples (for example single-use portion 140); and (3) an operative cannula that includes visualization as well as a working channel for performing one or more different types of surgical procedures.

Figure 9A:
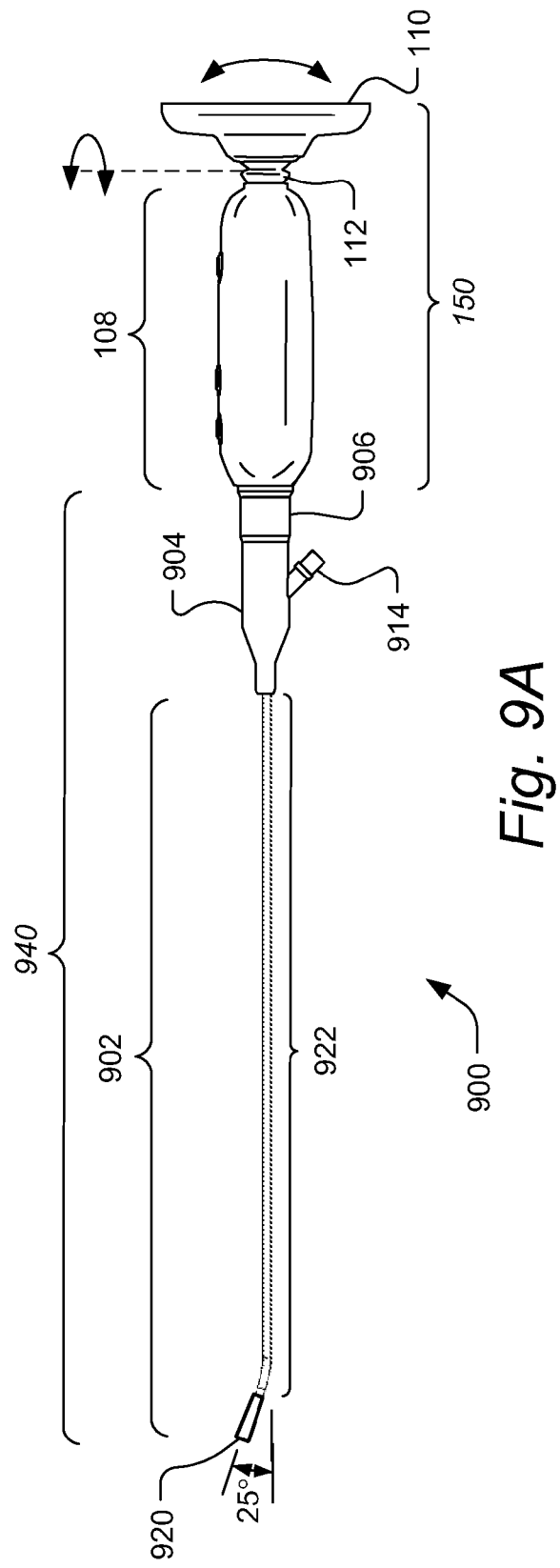

FIGS. 9A-9G illustrate a single-use portion that includes a cannula configured for fluid-in flow and visualization, according to some embodiments. As shown in FIG. 9A, the hysteroscopy device 900 comprises a single-use portion 940 with a sliding connector 906 that is configured to mate with re-useable portion 150 that has been shown and described elsewhere herein. The single use portion 940 also includes a fluid hub 904 having a single fluid port 914 that is in fluid communication with a single fluid lumen within shaft 922. Cannula 902 includes a shaft 922 and a distal tip 920 which includes one more forward facing in-flow ports, a camera module and LED lighting as will be described in further detail herein. FIG. 9B is a right side view of the shaft 922, and FIG. 9C is a cross section along A-A'. As can be seen in FIG. 9C, there is two lumens in shaft 922. Circular lumen 902 has an inner diameter of 1.5 mm that contains the electrical cable 980 between the distal tip 920 and the connector 906. Crescent-shaped fluid lumen 904 is in fluid communication with the fluid port 914 at the proximal end of shaft 922 and with forward facing in-flow ports on the distal tip 920. According to some embodiments, the cross sectional area of fluid lumen 904 is about 2.43 mm². Providing a hysteroscopy device having fluid in-flow capabilities with an outer diameter of less than about 4 mm has been found to be desirable, and according to even more preferred embodiments the outer diameter of shaft 922 is less than about 3.6 mm. In the example shown in FIG. 9C, the outer diameter of shaft 922 is 3.4 mm, and an outer wall thickness of 0.016 inches. FIG. 9D is a right side view showing further detail of the distal end of shaft 922, according to some embodiments. According to some embodiments, shaft 922 is constructed of a heat and UV stabilized nylon 12 grade for tube extrusion such as Grilamid® L25.

FIG. 9E is a left side view of the distal end of device 900, showing a separate distal tip shell 942 that surrounds a holder block 940. Shell 942 can be made, for example, of acrylic or other suitable material. The holder block 940 houses lens sensor stack 950 which can be of the same design as lens sensor stack 750 described herein. According to some embodiments, the distal tip shell 942 is tapered as shown such that the most distal end is of larger dimension than the proximal end (where it mates with the shaft 922). It has been found that providing a device with variable dimensions, in particular larger distal tip paired with a narrower shaft, allow for certain advantages in facilitating fluid management (which is described in greater detail with respect to FIG. 11), as well as providing for more frontal area for the front facing fluid ports, LEDs and camera module. According to some embodiments the diameter of the distal end of tip shell 942 is 4.0 mm. It has been found that a differential of 0.4 mm is beneficial for fluid management during many applications. FIG. 9F is a perspective view of the distal tip 920, and shows the lens 952, which may be covered by a glass cover, as well as two LEDs 930 and 932. Two forward facing in-flow fluid ports 934 and 936 are also provided on the distal end of tip 920 as shown, and are in fluid communication with the fluid lumen 904 in shaft 922 an also to fluid port 914 on fluid hub 904. FIG. 9G is a perspective view of holder block 940 which according to some embodiments is made of a suitable plastic material, such as liquid crystal polymer.

Figure 10:
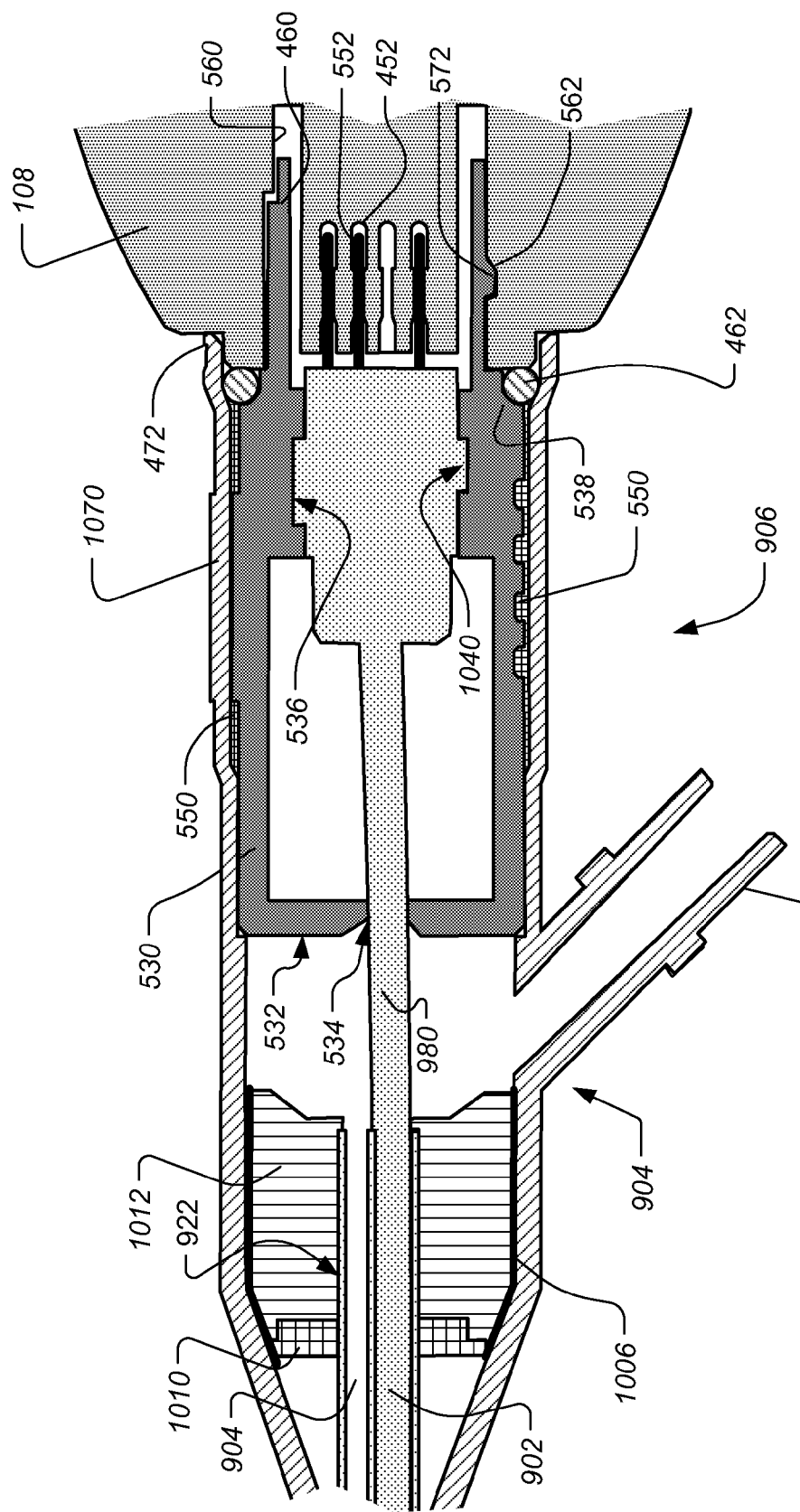
FIG. 10 is a cross section showing details of a sealed sliding connector for a device for hysteroscopy, according to some embodiments.

FIG. 10 is a cross section showing details of a sealed sliding connector for a device for hysteroscopy, according to some embodiments. As described, the sliding connector 906 is compatible with the re-useable handle 108. The fluid hub 904 and connector 906 are similar or identical to hub 104 and connector 106 in many respects other than being configured for only a single fluid-carrying lumen in the cannula shaft as well as a single fluid port on hub 904. A fluid cap 1010 and gasket 1012 that are shaped and positioned to provide fluid communication between lumen 904 shaft 922 to fluid port 914. According to some embodiments, transparent sealing glue 1006 is used between the outer shell of the fluid hub 904 and the cap 1010 and gasket 1012. The sliding connector 906 is shown here with an outer shell 1070 that includes a lip 472 that fits over an o-ring seal 462 and a protruding mating portion 460 of the handle assembly 108. Other seals can be provided along the length of connector 906 to further isolate handle 108 from patient matter and/or fluids that could otherwise contaminate and/or cause connection failure such as electrical failures on handle 108. The cable 980 carries video signals and control signals between the camera module and LEDs at distal tip 920 to connection pins housed within sleeve 460. The sleeve 460 fits into a closed channel on the handle 108 while the connection pins 552 mate with pin receptacles 452 as to form electrical connections the pins. The sliding connector 906 includes a barrier 530 that fits tightly inside outer shell 1070. According to some embodiments, a transparent sealing glue 550 is applied between the barrier 530 and shell 470. Barrier 530 terminates at its proximal end in an extended sleeve 460 that fits into a closed channel 560 in handle 108 such that an outwardly facing bump 572 releasably fits into an inward facing depression 562 in channel 560. Barrier 530 further includes a distal portion that terminates in a first seal 532 having an opening 534 through which cable 480 passes. An intermediate portion of barrier 530 provides an additional seal by including an inner indentation 536 tightly enveloping a radial projection 1040 of the proximal portion of cable 980. Barrier 530 further includes at its proximal portion a lip 538 that helps form another additional seal by bearing against o-ring 462 to further help ensure that fluid and tissue matter will not reach interior portions of handle 108 when the instrument is in use.

Figure 11:
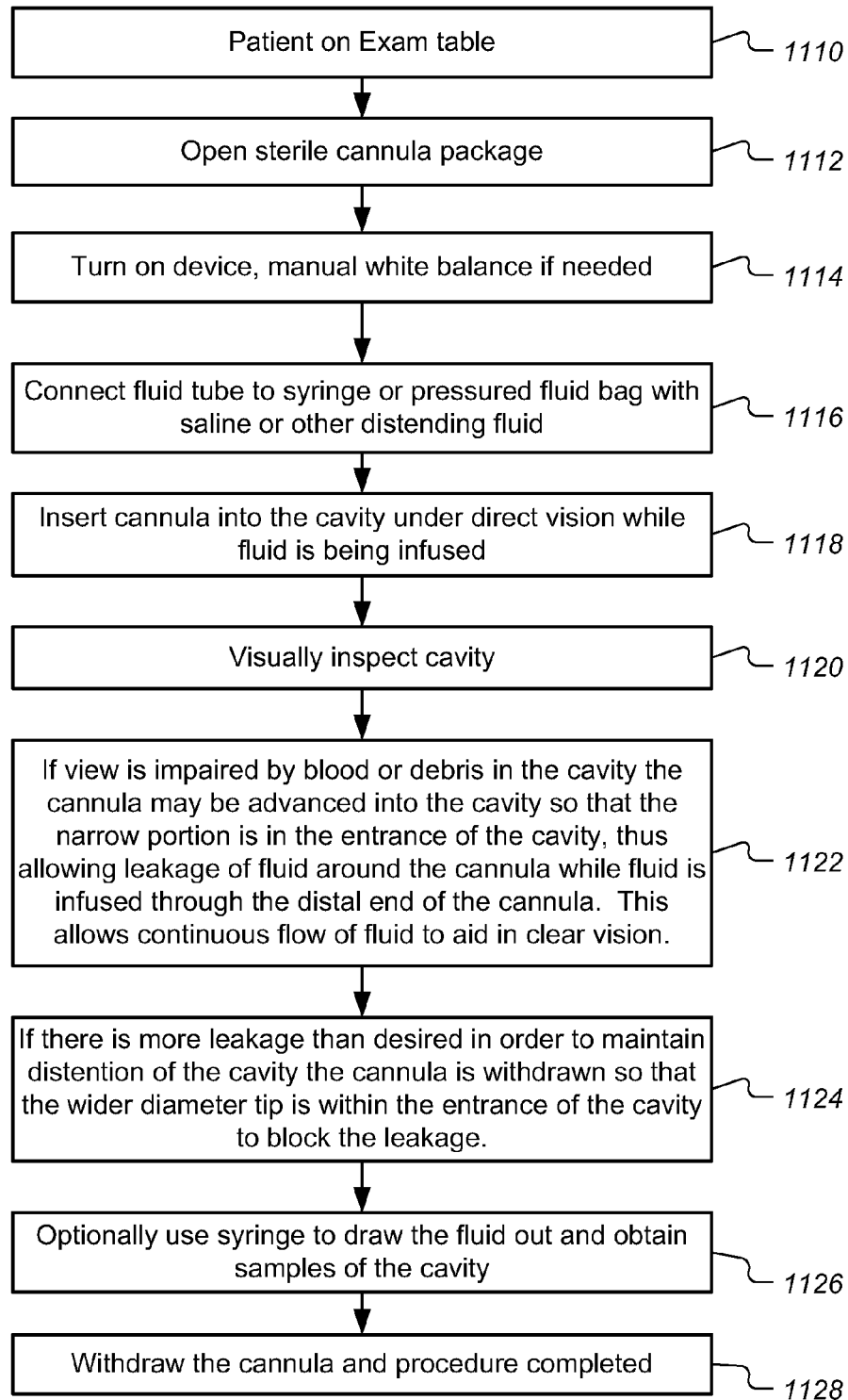
FIG. 11 is a flow chart showing aspects of using a variable dimension cannula for visual inspection of a patient's uterus, according to some embodiments.

FIG. 11 is a flow chart showing aspects of using a variable dimension cannula for visual inspection of a patient's uterus, according to some embodiments. The steps shown in FIG. 11 assume that a variable dimension cannula is being used for the visual inspection, such as cannula 902 in which the shaft of the cannula has a smaller diameter than the distal tip. By using a smaller shaft, fluid can be allowed to drain from the uterus. This is because after larger diameter tip is inserted through the cervix, the portion of the cannula that is in touch with the cervix is kept small which allows the fluid to drain.

In step 1110, the patient is on the exam table. In step 1112 the packaging enclosing the sterile single-use portion (e.g. portion 940 in FIG. 9A) is opened and the single-use portion is attached to the re-usable portion (e.g. portion 150 in FIGS. 1 and 9A). In step 1114 the device (e.g. device 900 in FIG. 9A) is turned on and a manual white balance procedure is carried out if desired or needed. In step 1116 a fluid tube and syringe or pressurized fluid bag containing saline or other distending fluid is attached to the fluid port of the device (e.g. port 914 in FIG. 9A). In step 1118, the distal end of the cannula is inserted into the cavity, such as a through the cervix to the uterus, under direct vision using the camera module and integrated display screen while fluid is being infused. In step 1120, the uterus is visually inspected, again under direct vision using the camera module and integrated display screen. In step 1122, if the view is impaired by blood or debris in the cavity the cannula can be advanced into the cavity so that the narrow portion is in the entrance (e.g. the cervix), thus allowing leakage of fluid around the cannula shaft while fluid is infused through the forward facing ports at the distal end of the cannula. This allows for continuous flow of fluid, which aids in obtaining improved visual images from the camera module. In step 1124, if the is more leakage than is needed in order to maintain the desired distension of the uterus, then the cannula can be withdrawn so that the wider diameter distal tip is within the entrance so as to effectively block a significant portion of leakage from the uterus. In step 1126, optionally, the syringe can be used to draw fluid out (out-flow) to obtain samples from the uterus. In step 1128, the cannula is withdrawn from the uterus and the procedure is completed. According to some embodiments, as mentioned in optional step 1126, sampling and/or biopsy can be carried out via the two forward facing ports on the distal end.

Conventional video endoscopes are typically either rigid or flexible. The rigid scopes have a rigid, non-bendable elongated body with a precision rod lens set inside as relay optics. On the other hand, flexible endoscopes are made of flexible elongated body. The tip portion of a flexible endoscope can be bendable or steerable by embedded cable wire that is attached to the levers at the proximal end. The rigid scope is rigidly attached to the scope body and handle so it can be moved in a fashion as a typical rigid body can be moved. On the other hand, the flexible endoscope is weakly coupled to the scope handle or body, and therefore has limited control by the handle and endoscope body. In either case, the handle or scope body has to be moved which is often undesirable.

According to some embodiments, a semi-flexible (or semi-rigid) endoscope is provided. In one embodiment, the elongated body (the scope cannula) can be easily manipulated spatially to achieve the best visualization of cavity such as a distended uterus or knee joint. Optimal flexibility (or stiffness/rigidity) of the cannula allow the operator clinician to bend or steer the cannula without moving the scope handle or scope body. For example, using a device such as device 100 of FIG. 1 or device 900 of FIG. 9A, the operator can use one hand to hold the handle 108, using one finger to control visualization using the LED lighting and/or snap buttons, while the operator uses the other hand to grasp the cannula at some intermediate point along the shaft (e.g. 5 inches from the distal tip) to bend and/or steer the cannula. According to some other embodiments, a selection from multiple cannulas having different lengths is made according to the size of the cavity which is being evaluated.

Figure 12A:
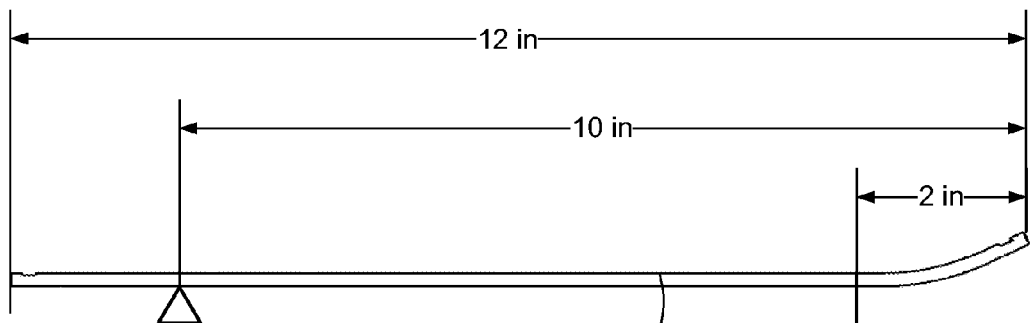
FIGS. 12A-12C illustrate a test setup to measure flexibility of a cannula shafts used in a device for hysteroscopy and/or combined hysteroscopy and endometrial biopsy, according to some embodiments.
Figure 12B:
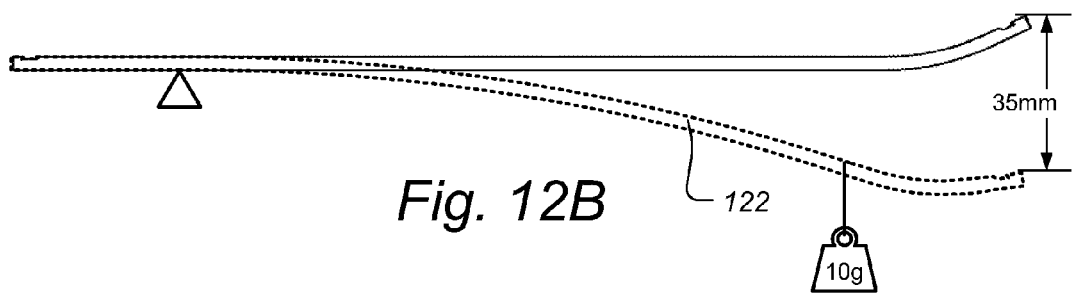
Figure 12C:
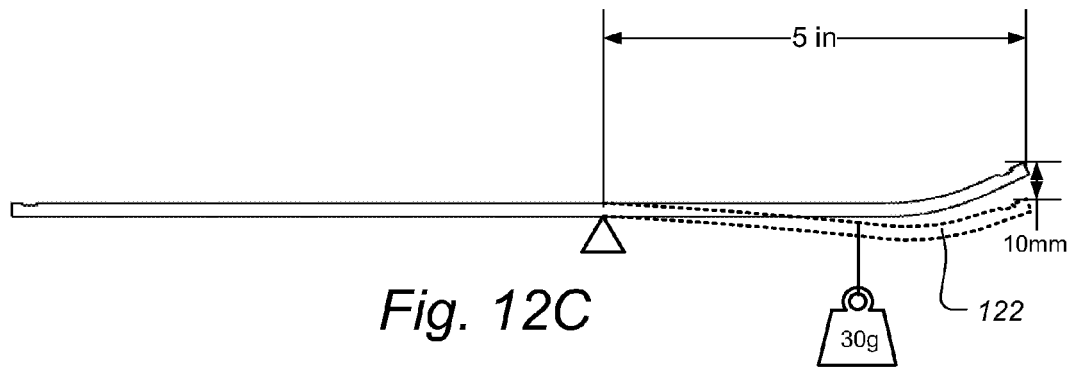

FIGS. 12A-12C illustrate a test setup to measure flexibility of a cannula shafts used in a device for hysteroscopy and/or combined hysteroscopy and endometrial biopsy, according to some embodiments. FIG. 12A shows a test set up in which the cannula shaft 122 is held firmly at a point 10 inches from the distal tip, while a force from a mass of 10 grams is applied to a point that is 2 inches from the distal dip. FIG. 12B shows shaft 122 in a bent state (in dotted lines) under the force applied as shown. In this example the distal tip was moved 35 mm from the applied force. FIG. 12C show the shaft 122 held at a different point, 5 inches from the distal tip, while a force from a different mass, 30 grams, is applied to a point 2 inches from the distal tip. In this example, the distal tip is deflected 10 mm under the applied force. Tables 1 and 2 show the tip deflections for a cannula shaft 122 which includes separated in-flow and out-flow fluid paths such as for shown in FIG. 6A. Table 1 shows the measured tip deflections when the shaft is held 10 inches from the distal tip and Table 2 shows the measured tip deflections when the shaft is held 5 inches from the distal tip.

TABLE 1

Cannula Having Separate In-flow and Out-flow Paths.
Held at 10 inches from distal tip, and loading
weight at 2 inches from distal tip.

| Weight (g) | Tip down (mm) |
| --- | --- |
| 10 | 35 |
| 20 | 70 |
| 30 | 100 |
| 40 | 130 |
| 50 | 145 |

TABLE 2

Cannula Having Separate In-flow and Out-flow Paths.
Held at 5 inches from distal tip, and loading
weight at 2 inches from distal tip.

| Weight (g) | Tip down (mm) |
| --- | --- |
| 10 | 2 |
| 20 | 6 |
| 30 | 10 |
| 40 | 14 |
| 50 | 17 |
| 70 | 25 |
| 90 | 35 |
| 100 | 39 |
| 150 | 60 |
| 170 | 70 |
| 200 | 80 |

Similarly, Tables 3 and 4 show the tip deflections for a cannula shaft 922 which includes a single fluid path such as for shown in FIG. 9B. Table 3 shows the measured tip deflections when the shaft is held 10 inches from the distal tip and Table 4 shows the measured tip deflections when the shaft is held 5 inches from the distal tip.

TABLE 3

Cannula Having Single Fluid Paths.
Held at 10 inches from distal tip, and loading
weight at 2 inches from distal tip.

| Weight (g) | Tip down (mm) |
|---|---|
| 5 | 75 |
| 10 | 100 |
| 15 | 135 |
| 20 | 150 |

TABLE 4

Cannula Having Single Fluid Path.
Held at 5 inches from distal tip, and loading
weight at 2 inches from distal tip.

| Weight (g) | Tip down (mm) |
|---|---|
| 5 | 4 |
| 10 | 8 |
| 15 | 13 |
| 20 | 18 |
| 30 | 26 |
| 40 | 32 |
| 50 | 41 |
| 70 | 55 |
| 90 | 70 |
| 100 | 75 |
| 120 | 85 |
| 150 | 95 |
| 170 | 100 |
| 200 | 105 |

It has been found that multiple fluid path cannulas having flexibilities of between 60% less deflection (i.e. more stiff), and 40% greater deflection (i.e. less stiff) than the examples shown in Tables 1-2 are suitable for many applications, according to some embodiments. More preferably, cannulas having multiple fluid paths should have flexibilities of between 30% less deflection and 25% greater deflection than the examples shown in Tables 1-2. Even more preferably, cannulas having multiple fluid paths should have flexibilities of between 15% less deflection and 10% greater deflection than the examples shown in Tables 1-2. It has been found that single fluid path cannulas having flexibilities of between 75% less deflection (i.e. more stiff), and 50% greater deflection (i.e. less stiff) than the examples shown in Tables 3-4 are suitable for many applications, according to some embodiments. More preferably, cannulas having a single fluid path should have flexibilities of between 50% less deflection and 25% greater deflection than the examples shown in Tables 3-4. Even more preferably, cannulas having a single fluid path should have flexibilities of between 25% less deflection and 10% greater deflection than the examples shown in Tables 3-4. Another advantage of providing flexibility and stiffness characteristics as described is a potential reduction in risks of injury such as by perforation of the uterine wall.

Figure 13:
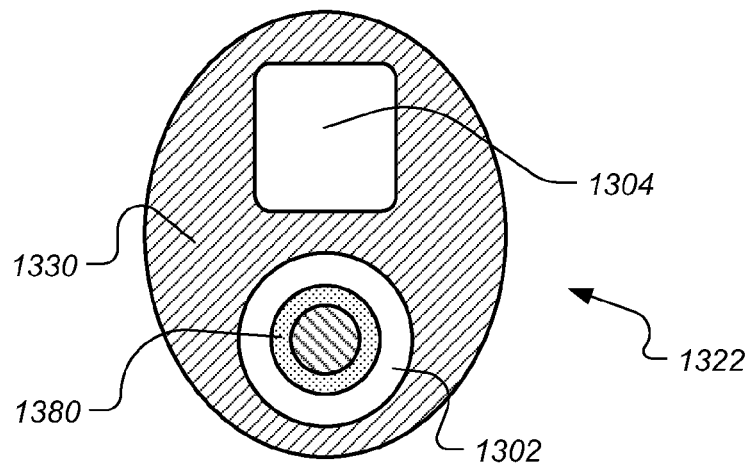
FIG. 13 is a cross section showing an example of a different internal shaft structures within a cannula for a device for hysteroscopy and/or combined hysteroscopy and endometrial biopsy, according to some embodiments.

Although internal shaft structures shown in FIGS. 6A, 6B, and 9C have been shown and described herein, other internal structures can be provided according to some other embodiments. FIG. 13 is a cross section showing an example of a different internal shaft structures within a cannula for a device for hysteroscopy and/or combined hysteroscopy and endometrial biopsy, according to some embodiments. In FIG. 13, cannula shaft 1322 includes two fluid lumens are provides for separated in-flow and out-flow channels. The wall 1330 defines and upper lumen 1304 that, for example can be used for out-flow, as well as a lower lumen 1302 that can be used for both in-flow as well as housing the electrical cable 1380 which is enclosed in a waterproof jacket.

Figure 14A:
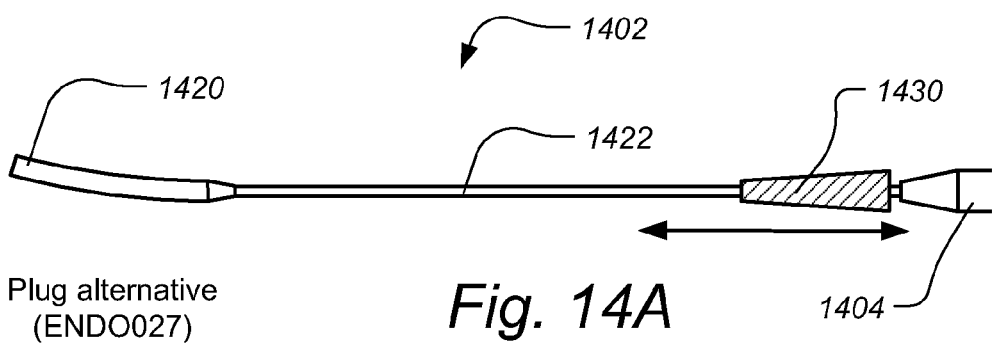
FIGS. 14A-14B illustrate aspects of a cannula for a device configured for combined hysteroscopy and endometrial biopsy, according to some alternative embodiments.
Figure 14B:
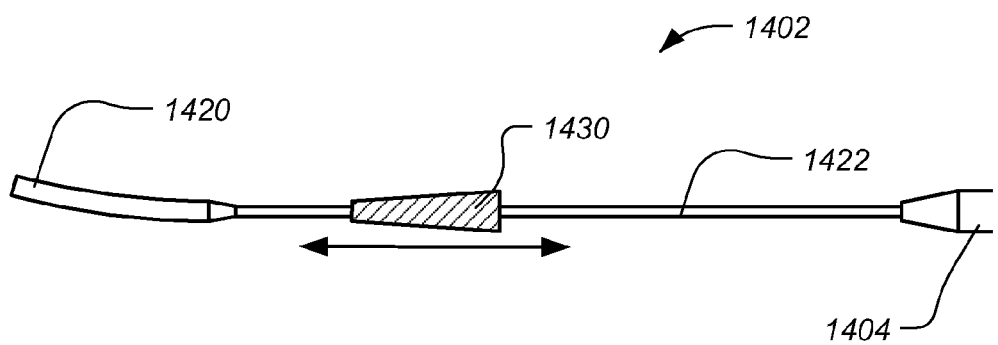

FIGS. 14A-14B illustrate aspects of a cannula for a device configured for combined hysteroscopy and endometrial biopsy, according to some alternative embodiments. A cannula 1402 is shown that has a variable diameter (a wider distal tip 1420 and narrower shaft 1422). The cannula 1402 also includes a fluid hub 1404 and sliding connector (not shown) that mates with a re-usable portion that can include a handle and integrated display screen (such as portion 150 in FIGS. 1 and 9A). In this case, for purposes of fluid management, a slideable sleeve 1430 is positioned surrounding cannula shaft 1422 can be used to plug the entrance of the body cavity to prevent fluid from draining out of the cavity. The sleeve 1430 can be a soft material and cylindrical in shape disposed such that is surrounds the cannula shaft 1422, or according to some embodiments sleeve 1430 can be a piece that can be mounted on the shaft 1422 after insertion of the tip 1420.

Figure 15C:
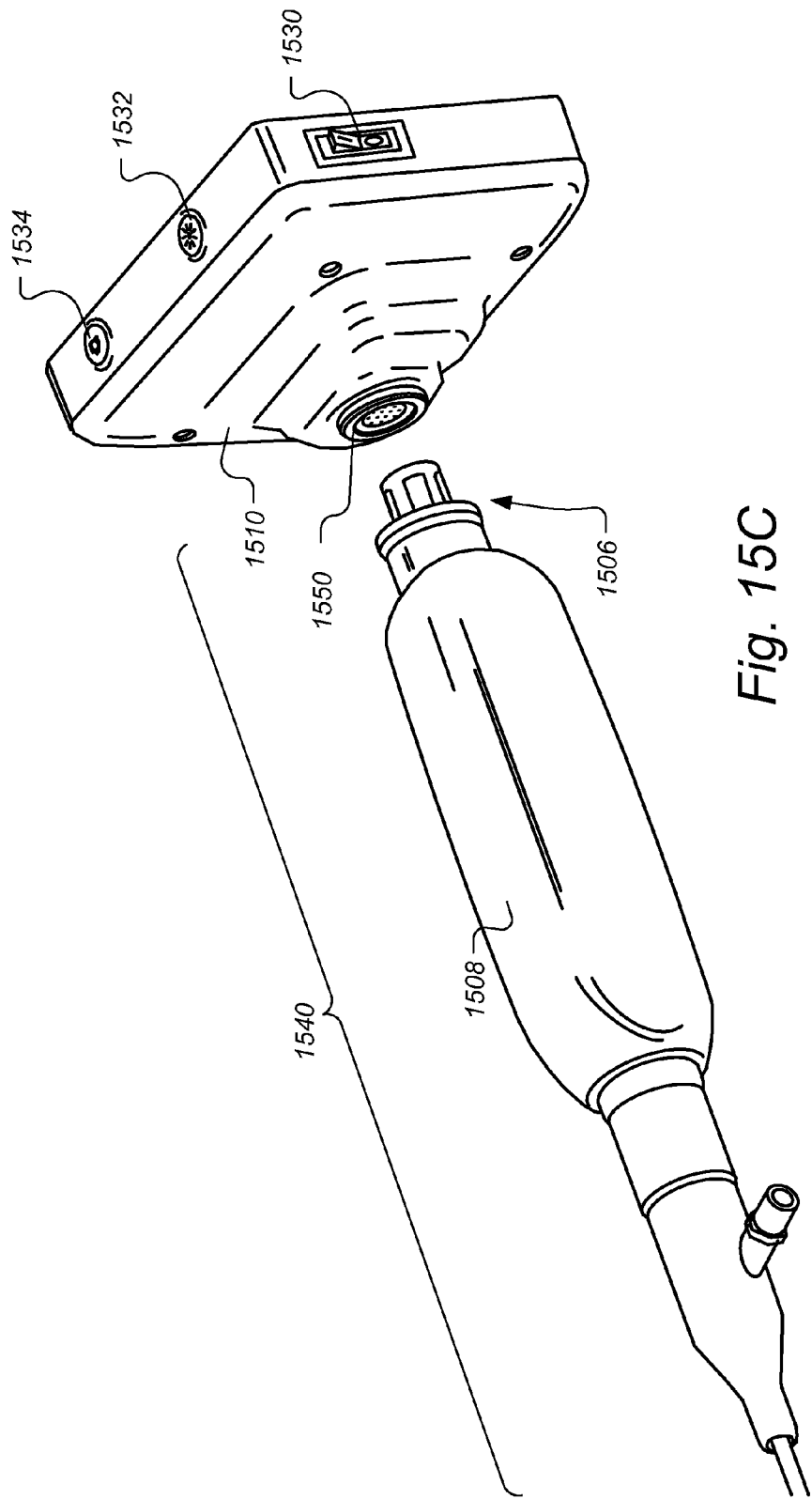

Although the junction between the single use portion 140 and the re-usable portion 150 is shown between the fluid hub and handle 108 in FIGS. 1 and 9A, according to some embodiments the junction can be positioned in other locations. It has been found that the most costly components of the endoscopic device are associated with the integrated display. As such, according to some embodiments, the single use portion can include the handle, while the re-usable portion includes the display. FIGS. 15A-15C illustrate a device for hysteroscopy and/or combined hysteroscopy and endometrial biopsy having a single use cannula, fluid hub and handle, and a re-usable display screen, according to some embodiments. FIGS. 15A and 15B show a device 1500 having a single use portion 1550 and a re-usable display screen 110 in a display screen assembly 1510. The single use portion includes: a cannula 102 that has a distal tip 120 and shaft 122; a fluid hub 140 that has a fluid port 114; a handle 1508 and a sliding connector 1506. According to some embodiments, the cannula 102 and fluid hub 104 can be as described herein with reference to FIGS. 1-5, 6A-F and 7A-C. According to some other embodiments the cannula and fluid hub can be identical or similar to the cannula 902 and fluid hub 904 shown in FIGS. 9A-G and 10. The handle 1508 can include the control buttons, electronics and battery, such as handle 108 described herein. According to some embodiments in-order to reduce the cost of the single-use portion 1550, some or all of the system electronics 1522 and/or the battery 1520 can be located in the display screen assembly 1510. A sliding connector 1506 forms a connection between the display assembly 1510 and the handle 1508. The sliding connector 1506 preferably includes some or all of the fluid barriers and seals described with respect to connector 106, in order to prevent fluid from entering mating portion of the connector 1506 and/or the system electronics and LCD display in display assembly 1510.

FIG. 15C is a perspective view of device 1500 with the sliding connector 1506 disconnected. The sliding connector mates with a connector 1550 on display assembly 1510. According to some embodiments, one or more of on/off button 1530, LED lighting control button 1532 and "snap" button 1534 can be located on the display assembly 1510 so that the user can control the device 1500 using hardware buttons, which may be easier to use with gloved or wet hands, for example, while maintaining a low-cost single-use portion 1550. According to some other embodiments, soft-buttons can be used on touch screen 110 on display assembly 1510.

Although the foregoing has been described in some detail for purposes of clarity, it will be apparent that certain changes and modifications may be made without departing from the principles thereof. It should be noted that there are many alternative ways of implementing both the processes and apparatuses described herein, including for using the described devices or certain aspects thereof for hysteroscopy but not for endometrial biopsy, or for endometrial biopsy but not for hysteroscopy, or for endoscopy and/or biopsy other than of the uterus. For example, in some applications the device shown in FIGS. 1-7C and 13-15C could also be used for taking fluid and/or fluid/tissue endometrial samples through the forward facing fluid parts. Accordingly, the present embodiments are to be considered as illustrative and not restrictive, and the body of work described herein is not to be limited to the details given herein, which may be modified within the scope and equivalents of the appended claims.

What is claimed is:

1. An integrated endoscopic instrument for examining a uterus of a patient, the integrated endoscopic instrument comprising:
   an elongate member having a proximal end, a distal end, and a shaft extending from the distal end to the proximal end,
      wherein the shaft defines a fluid channel and houses a plurality of electrical conductors,
      wherein the shaft has a first outer diameter of less than 5 mm, and the distal end has a second outer diameter that is greater than the first outer diameter, such that the elongate member can be advanced distally to position the distal end inside of the uterus and to position the shaft within a cervix of the patient for allowing fluid to leak from the uterus around the shaft and into the cervix, and such that the elongate member can be withdrawn proximally to position the distal end within the cervix for blocking leakage of fluid from the uterus to the cervix; and
      wherein the plurality of electrical conductors are configured to carry video signals and control signals;
   an imaging system at the distal end of the elongate member configured to image the uterus and to provide the video signals;
   an illumination system at the distal end of the elongate member configured to illuminate the uterus at an illumination field viewed by the imaging system;
   a distal facing fluid opening at the distal end of the elongate member and in fluid communication with the fluid channel, wherein the distal facing fluid opening is positioned to improve a visual inspection using the imaging system by delivering fluid to flow in a distal direction thereby clearing debris close to the imaging system;
   a handle that is configured and dimensioned to be grasped and manipulated by a user; and
   an integral image display that is electrically coupled to the imaging system by at least some of the plurality of electrical conductors, wherein the integral image display is configured to display images provided by the imaging system for viewing by the user.

2. An integrated endoscopic instrument according to claim 1, wherein the first outer diameter is less than 3.8 mm.

3. An integrated endoscopic instrument according to claim 2, wherein the second outer diameter is at least 0.4 mm greater than the first outer diameter.

4. An integrated endoscopic instrument according to claim 1, wherein the second outer diameter is greater than 3.5 mm.

5. An integrated endoscopic instrument according to claim 4, wherein the second outer diameter is at least 0.4 mm greater than the first outer diameter.

6. An integrated endoscopic instrument according to claim 1, wherein the distal end is an integral distal end.

7. An integrated endoscopic instrument according to claim 1, wherein the handle comprises control buttons and system electronics that actuate the imaging system and the illumination system.

8. An integrated endoscopic instrument according to claim 1, wherein the integral image display is mounted to the handle.

9. An integrated endoscopic instrument according to claim 1, wherein the elongate member, the handle, and the integral image display are positioned along a longitudinal axis defined by the shaft of the elongate member.

10. An integrated endoscopic instrument according to claim 1, wherein the elongate member, the handle, and the integral image display are coupled to one another such that the elongate member, the handle, and the integral image display move together when the handle is moved.

11. An integrated endoscopic instrument according to claim 1, wherein the integral image display is tiltable with respect to the handle.

\* \* \* \* \*